United States Patent
Miller et al.

(10) Patent No.: US 10,544,457 B2
(45) Date of Patent: Jan. 28, 2020

(54) METHODS AND COMPOSITIONS FOR ENRICHING COMPOSITIONS FOR POLYMERASE ENZYME COMPLEXES

(71) Applicant: Pacific Biosciences of California, Inc., Menlo Park, CA (US)

(72) Inventors: Erik Miller, Berkeley, CA (US); Keith Bjornson, Fremont, CA (US); Kristofor Nyquist, Oakland, CA (US); Satwik Kamtekar, Mountain View, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 175 days.

(21) Appl. No.: 15/618,535

(22) Filed: Jun. 9, 2017

(65) Prior Publication Data
US 2017/0356041 A1    Dec. 14, 2017

Related U.S. Application Data

(60) Provisional application No. 62/350,045, filed on Jun. 14, 2016.

(51) Int. Cl.
*C12Q 1/6874* (2018.01)
*C12N 9/96* (2006.01)
*C12N 9/12* (2006.01)

(52) U.S. Cl.
CPC ......... *C12Q 1/6874* (2013.01); *C12N 9/1241* (2013.01); *C12N 9/96* (2013.01)

(58) Field of Classification Search
None
See application file for complete search history.

(56) References Cited

U.S. PATENT DOCUMENTS

| | | |
|---|---|---|
| 5,001,050 A | 3/1991 | Blanco et al. |
| 5,034,506 A | 7/1991 | Summerton et al. |
| 5,198,543 A | 3/1993 | Blanco et al. |
| 5,235,033 A | 8/1993 | Summerton et al. |
| 5,328,824 A | 7/1994 | Ward et al. |
| 5,476,928 A | 12/1995 | Ward et al. |
| 5,576,204 A | 11/1996 | Blanco et al. |
| 6,451,591 B1* | 9/2002 | Edwards .......... C07K 1/12 422/500 |
| 6,917,726 B2 | 7/2005 | Levene et al. |
| 7,033,764 B2 | 4/2006 | Korlach et al. |
| 7,041,812 B2 | 5/2006 | Kumar et al. |
| 7,052,847 B2 | 5/2006 | Korlach et al. |
| 7,056,661 B2 | 6/2006 | Korlach et al. |
| 7,056,676 B2 | 6/2006 | Korlach et al. |
| 7,302,146 B2 | 11/2007 | Turner et al. |
| 7,315,019 B2 | 1/2008 | Turner et al. |
| 7,692,783 B2 | 4/2010 | Lundquist et al. |
| 7,715,001 B2 | 5/2010 | Lundquist et al. |
| 7,907,800 B2 | 3/2011 | Foquet et al. |
| 7,968,702 B2 | 6/2011 | Wegener et al. |
| 7,995,202 B2 | 8/2011 | Lundquist et al. |
| 8,658,365 B2* | 2/2014 | Bjornson et al. .... C12Q 1/6869 435/6.12 |
| 8,669,374 B2 | 3/2014 | Shen et al. |
| 8,802,600 B2 | 8/2014 | Rank et al. |
| 8,889,886 B2 | 11/2014 | Yue et al. |
| 8,906,612 B2 | 12/2014 | Shen et al. |
| 8,906,670 B2 | 12/2014 | Gray et al. |
| 8,936,911 B2 | 1/2015 | Sun et al. |
| 8,993,307 B2 | 3/2015 | Zaccarin et al. |
| 8,994,946 B2 | 3/2015 | McCaffrey et al. |
| 9,051,263 B2 | 6/2015 | Shen |
| 9,062,091 B2 | 6/2015 | Bjornson et al. |
| 9,223,084 B2 | 12/2015 | Grot et al. |
| 9,372,308 B1 | 6/2016 | Saxena et al. |
| 9,624,540 B2 | 4/2017 | Lundquist et al. |
| 9,658,161 B2 | 5/2017 | Saxena et al. |
| 2003/0044781 A1 | 3/2003 | Korlach et al. |
| 2003/0124576 A1 | 7/2003 | Kumar et al. |
| 2003/0174992 A1 | 9/2003 | Levene et al. |
| 2007/0036511 A1 | 2/2007 | Lundquist et al. |
| 2007/0072196 A1 | 3/2007 | Xu et al. |
| 2007/0188750 A1 | 8/2007 | Lundquist et al. |
| 2007/0196846 A1 | 8/2007 | Hanzel et al. |
| 2007/0206187 A1 | 9/2007 | Lundquist et al. |
| 2008/0030628 A1 | 2/2008 | Lundquist et al. |
| 2008/0032301 A1 | 2/2008 | Rank et al. |

(Continued)

FOREIGN PATENT DOCUMENTS

| | | |
|---|---|---|
| WO | WO 2007/041342 A2 | 4/2007 |
| WO | WO 2007/075987 A2 | 7/2007 |

(Continued)

OTHER PUBLICATIONS

Sano, T. et al. "Recombinant Core Streptavidins", Journal of Biological Chemistry, vol. 270, No. 47, p. 28204-28209 (1995).
Albà, M. "Protein Family Review: Replicative DNA Polymerases" Genome Biology 2(1):reviews 3002.1-3002.4 (2001).
Aoki A., "Microwell Cluster for Processing Electron Microscope Sections for Immunocytochemistry", Biotech. Histochem. 67: 98-9 (1992).
Burgers et al. "Eukaryotic DNA polymerases: proposal for a revised nomenclature" J Biol Chem. 276(47):43487-90 (2001).
Clackson et al. "Making antibody fragments using phage display libraries" Nature 352:624-628 (1991).
Crameri et al. "DNA shuffling of a family of genes from diverse species accelerates directed evolution" Nature 391:288-291 (1998).
Deng, T. et al., "Prototyping of Masks, Masters, and Stamps/Molds for Soft Lithography Using an Office Printer and Photographic Reduction", Anal, Chem. 72:3176-80 (2000).

(Continued)

Primary Examiner — Kaijiang Zhang
(74) Attorney, Agent, or Firm — Monicia Elrod-Erickson

(57) ABSTRACT

The present invention provides methods, compositions, and systems for enriching compositions for polymerase enzyme complexes. In particular, the methods, compositions, and systems of the present invention remove free polymerases from the compositions using one or more purification steps, including protease treatment, thus enriching the compositions for polymerases complexed with a template nucleic acid.

21 Claims, 4 Drawing Sheets

(56) References Cited

U.S. PATENT DOCUMENTS

| | | |
|---|---|---|
| 2008/0108082 A1 | 5/2008 | Rank et al. |
| 2009/0029385 A1 | 1/2009 | Christians et al. |
| 2009/0208957 A1 | 8/2009 | Travers et al. |
| 2009/0286245 A1 | 11/2009 | Bjornson et al. |
| 2009/0298075 A1 | 12/2009 | Travers et al. |
| 2010/0075332 A1 | 3/2010 | Patel et al. |
| 2010/0093555 A1 | 4/2010 | Bjornson et al. |
| 2010/0112645 A1 | 5/2010 | Clark et al. |
| 2010/0152424 A1 | 6/2010 | Korlach et al. |
| 2010/0167299 A1 | 7/2010 | Korlach |
| 2011/0059505 A1 | 3/2011 | Hanzel et al. |
| 2011/0189659 A1 | 8/2011 | Clark et al. |
| 2012/0014837 A1 | 1/2012 | Fehr et al. |
| 2012/0019828 A1 | 1/2012 | McCaffrey et al. |
| 2012/0021525 A1 | 1/2012 | Fehr et al. |
| 2012/0034602 A1 | 2/2012 | Emig et al. |
| 2012/0052506 A1 | 3/2012 | Yue et al. |
| 2012/0058469 A1 | 3/2012 | Shen |
| 2012/0077189 A1 | 3/2012 | Shen et al. |
| 2012/0085894 A1 | 4/2012 | Zhong et al. |
| 2013/0217007 A1 | 8/2013 | Kamtekar et al. |
| 2013/0316912 A1 | 11/2013 | Bjornson et al. |
| 2013/0327644 A1 | 12/2013 | Turner et al. |
| 2014/0051068 A1 | 2/2014 | Cherf et al. |
| 2014/0094374 A1 | 4/2014 | Kamtekar et al. |
| 2014/0199016 A1 | 7/2014 | Grot et al. |
| 2014/0287964 A1 | 9/2014 | Lundquist et al. |
| 2015/0050659 A1 | 2/2015 | Lubomir et al. |
| 2015/0065353 A1 | 3/2015 | Turner et al. |
| 2017/0159119 A1 | 6/2017 | Sheikholeslami et al. |

FOREIGN PATENT DOCUMENTS

| | | | | |
|---|---|---|---|---|
| WO | WO 2007/076057 A2 | 7/2007 | | |
| WO | WO 2007/123763 A2 | 11/2007 | | |
| WO | WO-2007123763 A2 * | 11/2007 | .......... | B01J 19/0046 |
| WO | WO 2009/114182 A2 | 9/2009 | | |

OTHER PUBLICATIONS

Driscoll, R. J., et al., Atomic-Scale Imaging of DNA Using Scanning Tunneling Microscopy. Nature, 346(6281): 294-296 (1990).

Eid, J. et al., "Real-time DNA sequencing from single polymerase molecules", Science, 323(5910), 133-138 (2009).

Franklin, M. et al., Structure of the Replicating Complex of a Pol α Family DNA Polymerse, et al., Cell, vol. 105, 657-667, 2001.

Gibbs et al. "Degenerate oligonucleotide gene shuffling (DOGS): a method for enhancing the frequency of recombination with family shuffling" Gene 271:13-20 (2001).

Goodwin, P. M., et al., "Application of Single Molecule Detection to DNA Sequencing", Nucleosides & Nucleotides, 16(5-6): 543-550 (1997).

Hiraga and Arnold General method for sequence-independent site-directed chimeragenesis: J. Mol. Biol. 330:287-296 (2003).

Howorka, S., et al., "Sequence-Specific Detection of Individual DNA Strands using Engineered Nanopores", Nature Biotechnology, 19(7): 636-639 (2001).

Hübscher et al. "Eukaryotic DNA Polymerases" Annual Review of Biochemistry vol. 71: 133-163 (2002).

Kane et al., Patterning Proteins and Cells Using Soft Lithography, Biomaterials. 20: 2363-76 (1999).

Korlach et al. "Long, Processive Enzymatic DNA Synthesis Using 100% Dye-Labeled Terminal Phosphate-Linked Nucleotides", (2008) Nucleosides, Nucleotides and Nucleic Acids 27:1072-1083.

Korlach et al. "Selective Aluminum Passivation for Targeted Immobilization of Single DNA Polymerase Molecules in Zero-Mode Waveguide Nanostructures", (2008) PNAS U.S.A. 105(4):1176-1181.

Levene, et al., "Zero-mode waveguides for single-molecule analysis at high concentrations", Science 299:682-686, Jan. 2003.

Lundquist et al., "Parallel Confocal Detection of Single Molecules in Real Time", Optics Letters, vol. 33, Issue 9, pp. 1026-1028.

Meijer et al. "φ29 Family of Phages" Microbiology and Molecular Biology Reviews, 65(2):261-287 (2001).

Melissis, S. et al. "One-Step Purification of Taq DNA Polymerase Using Nucleotide-Mimetic Affinity Chromatography", Biotechnol. J., 2, 121-132, 2007.

Meller, A., et al., Rapid Nanopore Discrimination Between Single Polynucleotide Molecules, Proceedings of the National Academy of Sciences of the United States of America, 97(3): 1079-1084 (2000).

Novak, R., et al., "The Resistance of Ribonucleic Acid Polymerase to Proteolytic Attack during Transcription in Vitro", J. Biol. Chem., v. 243, p. 6068-6075 (1968).

Park & Marqusee, "Probing the High Energy States in Proteins by Proteolysis", J. Mol. Biol. (2004) 343, 1467-1476.

Park & Marqusee, "Quantitative Determination of Protein Stability and Ligand Binding by Pulse Proteolysis", Current Protocols in Protein Science (2006) 20.11.1-20.11.14.

Park & Marqusee, "Energetics-Based Protein Profiling on a Proteomic Scale: Identification of Proteins Resistant to Proteolysis", J. Mol. Biol. (2007) 368, 1426-1437.

Rigler, et al., DNA-Sequencing at the Single Molecule Level, Journal of Biotechnology, 86(3): 161 (2001).

Steitz "DNA polymerases: structural diversity and common mechanisms" J Biol Chem 274:17395-17398 (1999).

Wildes, D., et al., "Hydrogen Exchange and Ligand Binding: Ligand-Dependent and Ligand-Independent Protection in the Src SH3 Domain", Protein Science (2005) 14:81-88.

Zhu et al., "Analysis of Yeast Protein Kinases Using Protein Chips", Nat. Genet. 26:283-9 (2000).

* cited by examiner

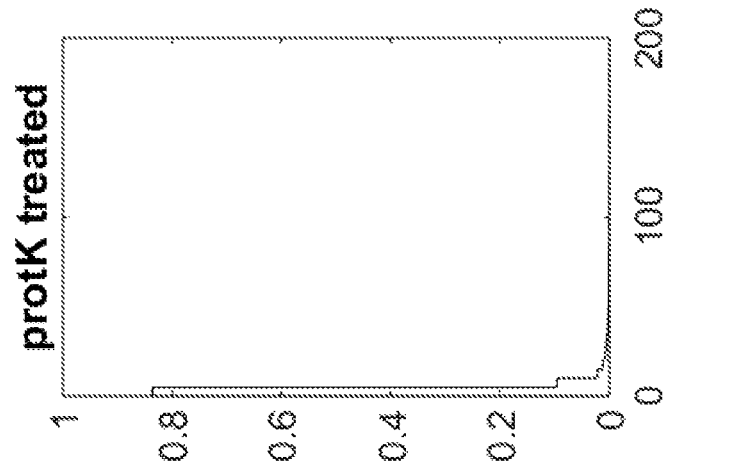
FIG. 1A  FIG. 1B  FIG. 1C
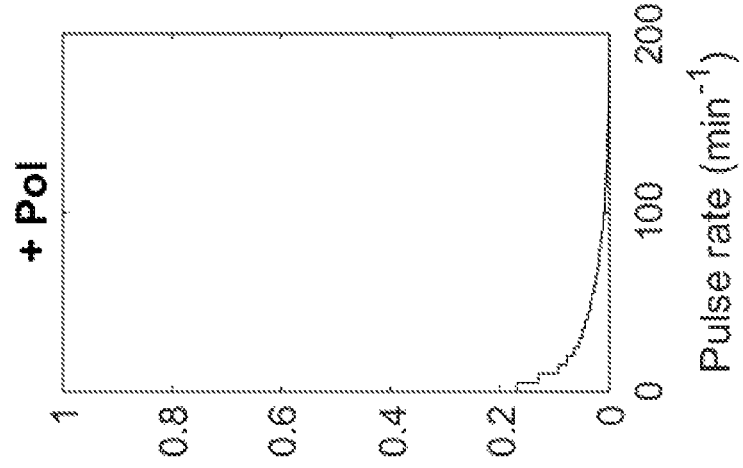
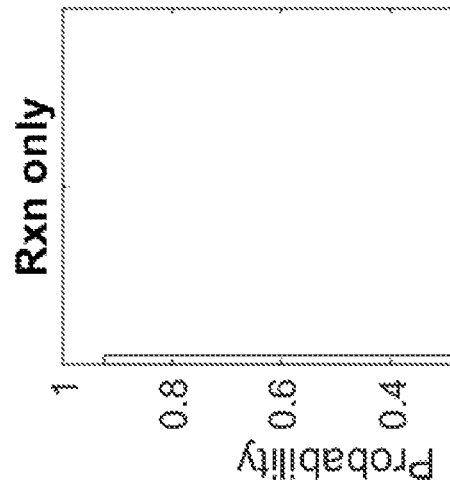

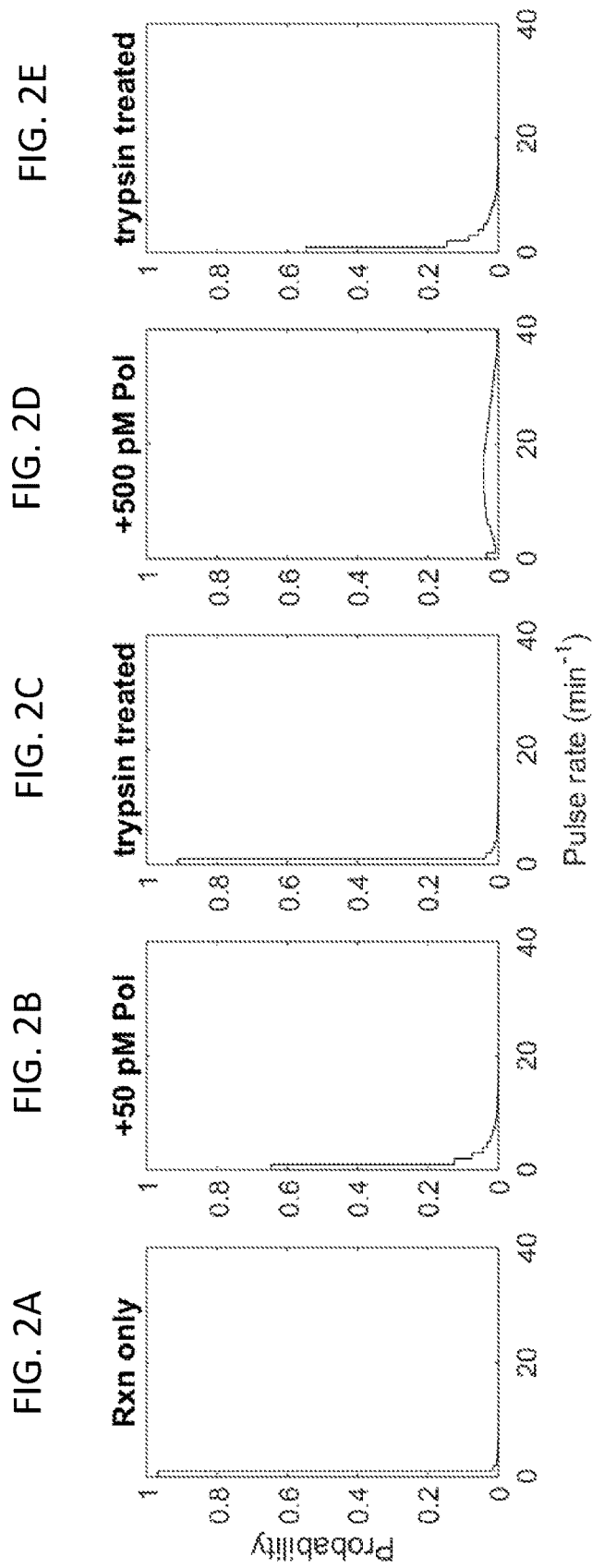

METHODS AND COMPOSITIONS FOR ENRICHING COMPOSITIONS FOR POLYMERASE ENZYME COMPLEXES

BACKGROUND OF THE INVENTION

Techniques in molecular biology and molecular medicine often rely on analysis of single biological molecules. Such techniques include DNA and RNA sequencing, polymorphism detection, the detection of proteins of interest, the detection of protein-nucleic acid complexes, and many others. The high sensitivity, high throughput and low reagent costs involved in single molecule analysis make it an increasingly attractive approach for a variety of detection and analysis problems in molecular medicine, from low cost genomics to high sensitivity marker analysis.

The small observation volumes used for single molecule nucleic acid sequencing and other analysis methods are typically provided by immobilizing or otherwise localizing the polymerase (or other) enzyme within an optical confinement reaction/observation region, such as an array of nanoscale wells, such as in an array of Zero Mode Waveguides (ZMWs), and delivering a template, primers, etc., to the reaction region. While these methods of nucleic acid sequencing are providing dramatic improvements in the ability to obtain sequence information, there is a need for improvements in the throughput and yield of the systems.

It is desirable to develop methods and compositions for enriching compositions for polymerase enzymes properly complexed with nucleic acid templates to provide sequencing data and to minimize the number of free polymerases in the composition that is eventually used for sequencing reactions. The present invention provides these and other features that will be apparent upon complete review of the following.

SUMMARY OF THE INVENTION

Accordingly, the present disclosure provides methods, compositions, and systems for enriching loading compositions containing free polymerases and polymerase enzyme complexes for polymerase enzyme complexes.

In one aspect, the present disclosure provides a method for enriching a loading composition for polymerase enzyme complexes in which the method includes the steps of: (a) providing a loading composition comprising (i) polymerase enzyme complexes, (ii) free polymerases, (iii) at least one non-catalytic metal ion, and (iv) a first set of one or more nucleotides or nucleotide analogs, wherein each polymerase enzyme complex comprises a polymerase enzyme, a template nucleic acid, and optionally a replication initiating moiety; (b) applying a protease to the loading composition to remove free polymerases, thus enriching the loading composition for polymerase enzyme complexes; and (c) distributing the loading composition onto a substrate. In some embodiments, the loading composition is purified to enhance the reaction mixture for polymerase enzyme complexes. In further embodiments, the applying step (b) is conducted after distributing step (c).

In further embodiments and in accordance with the above, the method for enriching a loading composition for polymerase enzyme complexes utilizes a protease comprising an endopeptidase or trypsin.

In yet further embodiments and in accordance with any of the above, the methods described herein utilize a substrate that includes an array of nanoscale wells.

In still further embodiments and in accordance with any of the above, the distributing step (c) includes immobilizing the polymerase enzyme complexes to the substrate.

In still further embodiments and in accordance with any of the above, the polymerase enzyme complexes include a reactive element, and the immobilizing occurs through an interaction of the reactive element and a binding site on the substrate. In yet further embodiments, the reactive element includes streptavidin and the binding site includes biotin. In still further embodiments, the reactive element is resistant to cleavage by the protease.

In still further embodiments and in accordance with any of the above, the at least one non-catalytic metal ion includes a member selected from the group consisting of strontium, cobalt, tin, calcium, nickel, europium, barium, iron, and zinc.

In still further embodiments and in accordance with any of the above, the substrate further includes a composition containing a protease inhibitor.

In still further embodiments and in accordance with any of the above, the methods described herein include a step (d) determining a nucleotide sequence of at least a portion of the template. In yet further embodiments, determining the nucleotide sequence includes the steps of: (i) providing a sequencing reaction mixture to the substrate, the sequencing reaction mixture comprising (i) at least one catalytic metal ion, and (ii) a second set of one or more nucleotides or nucleotide analogs; (ii) performing a polymerization reaction in which the polymerase replicates at least a portion of the template in a template-dependent manner, whereby one or more nucleotides or nucleotide analogs from the second set are incorporated into the resulting nucleic acid; and (iii) identifying a time sequence of incorporation of the one or more nucleotides or nucleotide analogs into the resulting nucleic acid.

In still further embodiments and in accordance with any of the above, the second set of one or more nucleotides or nucleotide analogs includes labeled nucleotides or nucleotide analogs.

In still further embodiments and in accordance with any of the above, the replication initiating moiety includes a primer hybridized to the template nucleic acid.

In a further aspect, the disclosure herein provides a method for enriching a loading composition for polymerase enzyme complexes, the method including the steps of: (a) providing a loading composition comprising (i) polymerase enzyme complexes, (ii) free polymerases, (iii) at least one non-catalytic metal ion, and (iv) a first set of one or more nucleotides or nucleotide analogs, wherein each polymerase enzyme complex comprises a polymerase enzyme, a template nucleic acid, and optionally a replication initiating moiety; (b) distributing the loading composition onto a substrate to provide a loaded substrate; and (c) applying a protease to the loaded substrate to remove free polymerases, thus enriching the loading composition for polymerase enzyme complexes. In further embodiments, the loading composition is purified to enhance the loading composition for polymerase enzyme complexes.

In a further aspect, the disclosure herein provides a method for enriching a loading composition for polymerase enzyme complexes, the method comprising: (a) providing a loading composition comprising free polymerases and polymerase enzyme complexes, wherein the polymerase enzyme complexes are in an inactive form; (b) applying a protease to the loading composition to remove free polymerases, thus enriching the loading composition for polymerase enzyme complexes; and (c) distributing the loading composition onto a substrate to provide a loaded substrate. In further embodiments, the inactive form of the polymerase enzyme complexes is maintained by including a non-catalytic metal ion in the loading composition. In yet further embodiments, the non-catalytic metal ion is a member selected from the group consisting of: strontium, cobalt, tin, calcium, nickel, europium, barium, iron, and zinc.

In further embodiments and in accordance with any of the above, the inactive form of the polymerase enzyme complexes is maintained by including at least one non-hydrolyzable nucleotide analog in the loading composition.

In further aspects, the disclosure herein provides a method of sequencing a nucleic acid template, the method comprising: exposing a composition comprising a polymerase enzyme complex to a protease in the presence of a non-catalytic metal ion and a first set of one or more nucleotides or nucleotide analogs; then removing or inactivating the protease; and then determining a nucleotide sequence of at least a portion of the template. In further embodiments, determining the nucleotide sequence includes providing a catalytic metal ion. In still further embodiments, determining the nucleotide sequence includes providing a second set of one or more nucleotides or nucleotide analogs; performing a polymerization reaction in which the polymerase replicates at least a portion of the template in a template-dependent manner, whereby one or more nucleotides or nucleotide analogs from the second set are incorporated into the resulting nucleic acid; and identifying a time sequence of incorporation of the one or more nucleotide or nucleotide analogs into the resulting nucleic acid. In yet further embodiments, prior to the determining step, the complex is immobilized on a substrate.

In further aspects, the disclosure herein provides a method of sequencing a nucleic acid template, the method comprising: exposing a composition comprising a polymerase enzyme complex to a protease in the presence of a non-hydrolyzable nucleotide analog; then removing or inactivating the protease; and then determining a nucleotide sequence of at least a portion of the template. In further embodiments, determining the nucleotide sequence includes providing a catalytic metal ion.

In further embodiments and in accordance with any of the above, determining the nucleotide sequence includes providing a set of one or more nucleotides or nucleotide analogs; performing a polymerization reaction in which the polymerase replicates at least a portion of the template in a template-dependent manner, whereby the one or more nucleotides or nucleotide analogs are incorporated into the resulting nucleic acid; and identifying a time sequence of incorporation of the one or more nucleotide or nucleotide analogs into the resulting nucleic acid. In further embodiments, the second set of one or more nucleotide or nucleotide analogs includes labeled nucleotides or nucleotide analogs.

In further embodiments and in accordance with any of the above, prior to the determining step, the complex is immobilized on a substrate.

In further embodiments and in accordance with any of the above, prior to the exposing step, the complex is immobilized on a substrate.

In further embodiments and in accordance with any of the above, the substrate includes an array of nanoscale wells.

In further embodiments and in accordance with any of the above, the polymerase enzyme complexes include a reactive element, and the immobilizing occurs through an interaction of the reactive element and a binding site on the substrate.

In further embodiments, the reactive element includes streptavidin and the binding site includes biotin.

In further embodiments and in accordance with any of the above, the composition undergoes a purification step to remove free polymerases that are not part of complexes. In yet further embodiments, the purification step includes size exclusion chromatography.

In further embodiments and in accordance with any of the above, the protease comprises an endopeptidase or trypsin.

In further embodiments and in accordance with any of the above, the determining is conducted in the presence of a protease inhibitor.

BRIEF DESCRIPTION OF THE DRAWINGS

FIG. 1A-FIG. 1C shows data on background sequencing pulse rates from compositions containing no polymerase (FIG. 1A), after addition of free polymerase (FIG. 1B), and then after treatment with Proteinase K (FIG. 1C).

FIG. 2A-FIG. 2E shows data on background sequencing pulse rates from compositions containing no polymerase (FIG. 2A), after addition of 50 pM free polymerase (FIG. 2B), and after treatment with trypsin (FIG. 2C). FIG. 2D shows background sequencing pulse rates from compositions containing 500 pM polymerase before treatment with trypsin, and FIG. 2E shows pulse rates after that same 500 pM polymerase composition was treated with trypsin.

DETAILED DESCRIPTION OF THE INVENTION

Figure 3:
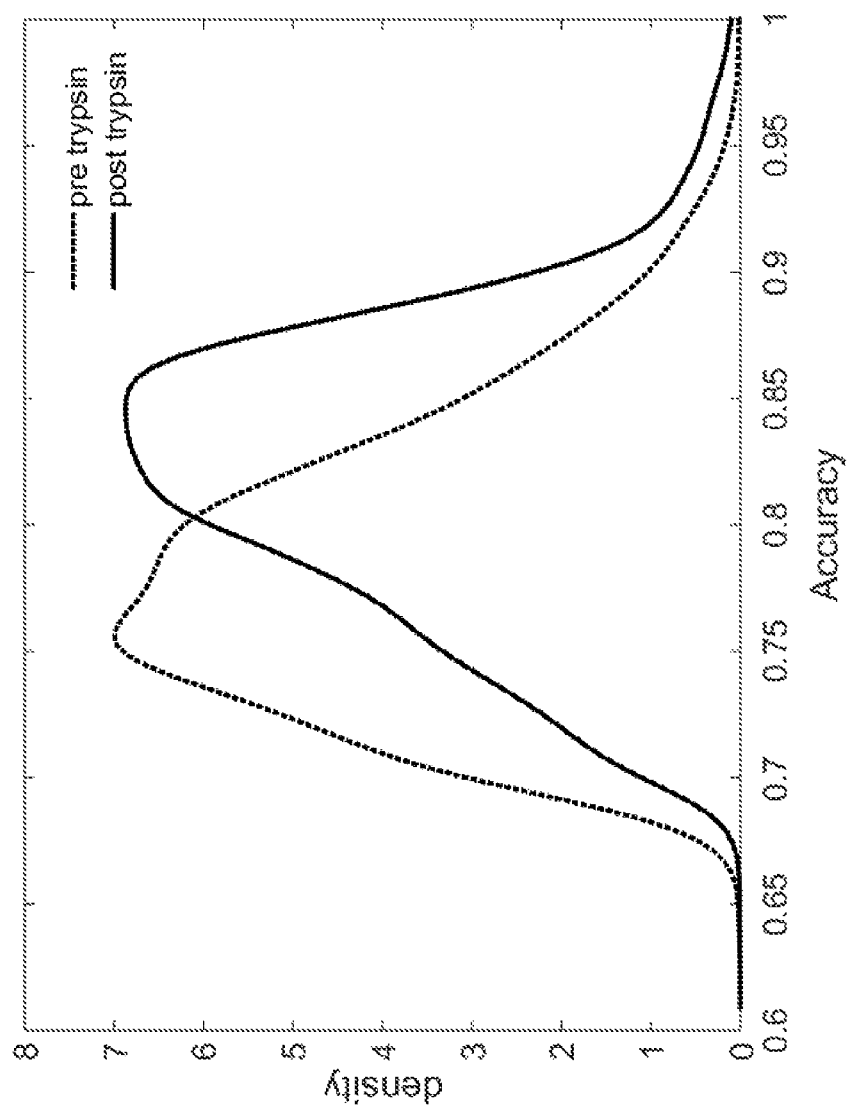
FIG. 3 shows raw accuracy of sequencing data from polymerase compositions on a substrate before (dashed line) and after (solid line) treatment with trypsin.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, phage display, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, N.Y., Gait, "*Oligonucleotide Synthesis: A Practical Approach*" 1984, IRL Press, London, Nelson and Cox (2000), *Lehninger, Principles of Biochemistry* $3^{rd}$ Ed., W. H. Freeman Pub., New York, N.Y. and Berg et al. (2002) *Biochemistry*, $5^{th}$ Ed., W. H. Freeman Pub., New York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this invention. Accordingly, it is intended that the methods and compositions can include additional steps and components (comprising) or alternatively including steps and compositions of no significance (consisting essentially of) or alternatively, intending only the stated method steps or compositions (consisting of).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

By "nucleic acid" or "oligonucleotide" or grammatical equivalents herein means at least two nucleotides covalently linked together. A nucleic acid of the present invention will generally contain phosphodiester bonds, although in some cases, nucleic acid analogs are included that may have alternate backbones, comprising, for example, phosphoramide, phosphorothioate, phosphorodithioate, and peptide nucleic acid backbones and linkages. Other analog nucleic acids include those with positive backbones; non-ionic backbones, and non-ribose backbones, including those described in U.S. Pat. Nos. 5,235,033 and 5,034,506. The template nucleic acid may also have other modifications, such as the inclusion of heteroatoms, the attachment of labels, such as dyes, or substitution with functional groups which will still allow for base pairing and for recognition by the enzyme.

As used herein, a "substantially identical" nucleic acid is one that has at least 80%, 85%, 90%, 95%, 96%, 97%, 98% or 99% A sequence identity to a reference nucleic acid sequence. The length of comparison is preferably the full length of the nucleic acid, but is generally at least 20 nucleotides, 30 nucleotides, 40 nucleotides, 50 nucleotides, 75 nucleotides, 100 nucleotides, 125 nucleotides, or more.

I. Overview

The present invention is directed to methods, devices, compositions and systems for enriching loading compositions containing a mixture of free polymerases and polymerase enzyme complexes for those polymerase enzyme complexes. "Loading compositions" are any composition that can be added to or distributed on a substrate. The term "polymerase enzyme complexes" as used herein refers to complexes comprising a template nucleic acid molecule, a polymerase enzyme, and optionally a replication initiating moiety. The replication initiating moiety can be a standard oligonucleotide primer, or, alternatively, a component of the template, e.g., the template can be a self-priming single stranded DNA, a nicked double stranded DNA, or the like. Similarly, a terminal protein can serve as the replication initiating moiety.

Enrichment of loading compositions for polymerase enzyme complexes is beneficial for various applications, for example, in single molecule sequencing. Free polymerases (polymerases that are not complexed with nucleic acid templates) can bind fluorescent substrates and cause extra pulses during single molecule sequencing reactions. Such extra pulses can be mistaken for nucleotide incorporation events and thus decrease accuracy of sequence determination and/or can increase background noise. Free polymerases can also compete for space within substrate reaction regions with the desired enzymes correctly localized to the primer terminus, thus preventing accurate sequencing reads from enzymes that are able to provide such reads through, for example, sequencing by synthesis reactions. Enhancing the amount of polymerase enzyme complex and minimizing the amount of free polymerase therefore provides benefits such as, e.g., increased raw accuracy of sequence reads and improved signal to noise ratio in sequencing data.

In general, enrichment of loading compositions for polymerase enzyme complexes is accomplished by removing or otherwise isolating free polymerases from the remainder of the components of the loading compositions, thereby enriching the loading compositions for the polymerase enzyme complexes. Loading compositions can include a mixture of free polymerases and polymerase enzyme complexes as well as other components, including without limitation nucleotides, nucleotide analogs, non-catalytic metal ions, buffers, and any combination thereof.

In certain examples, the enrichment of the loading composition for the polymerase enzyme complexes is accomplished by applying a protease to the loading composition to remove the free polymerases. Without being bound to a particular mechanism of action, one potential source for the differential effect of the protease on free polymerases versus polymerases that are part of complexes is that free polymerases are in a more open structural configuration that allows access for the degradative effects of the protease. In contrast, polymerases that are complexed with nucleic acids tend to be in a more closed tightly bound form that is able to resist protease digestion. Proteases of use in the methods disclosed herein include without limitation endopeptidases, including for example trypsin, proteinase K, chymotrypsin, pepsin, papain, thermolysin, and elastase.

In further examples, the protease is added to the loading composition prior to addition of the loading composition to any type of substrate—in other words, the protease is added in the bulk loading composition, which is in some situations a solution, prior to distribution of that loading composition onto a surface. In some examples, the loading composition is first added to a substrate and then the protease is also added to the substrate to remove free polymerases on the surface. In either method, removal of the free polymerases has the advantage of reducing background noise from the activity of free polymerases during subsequent reactions, including sequencing reactions.

In certain examples, the loading composition is subjected to a purification step to also assist with the enrichment of the loading composition for polymerase enzyme complexes. In certain situations, the free polymerases are removed through magnetic bead capture. In some situations, the purification steps are based on size-exclusion technologies that isolate free polymerases from the larger polymerase enzyme complexes. Any size exclusion technologies known in the art can be used for such methods, including size exclusion chromatography, such as those utilized in spin columns.

In further examples, the loading composition is subjected to multiple enrichment steps, including both a protease application and a size exclusion purification treatment. As will be appreciated, these multiple enrichment steps can occur in any order and at any point of a workflow involving distributing a loading composition onto a substrate. For example, the loading composition may be subjected to a protease treatment prior to a size exclusion purification treatment, or vice versa. In addition, the loading composition may be subjected to multiple treatments—i.e., multiple protease applications and/or multiple size exclusion purification steps. In still further examples, the loading composition is first distributed onto a substrate and is then subjected to a protease treatment while on the substrate. In yet further examples, the loading composition undergoes a size exclusion purification step, is then distributed onto a substrate, and is then subjected to a protease treatment. As yet another example, the loading composition is subjected to protease treatment, undergoes a size exclusion purification step, and is then distributed onto a substrate. As a further example, the loading composition is subjected to protease treatment, undergoes a size exclusion purification step, is then distributed onto a substrate, and is then subjected to a second protease treatment. As will be appreciated, any of these above described methods can be altered in terms of order and number of steps taken for enriching the loading composition for polymerase enzyme complexes.

In certain examples, after treatment with a protease (with or without a size exclusion purification step), a protease inhibitor is added to the loading composition (or to the substrate if the loading composition has been distributed on a substrate). The protease inhibitor will halt the activity of the protease or otherwise inactivate the protease to prevent further degradation of components of the loading composition. Use of a protease inhibitor may also prevent interference with any subsequent reactions with the components of the loading composition—for example, any subsequent sequencing reactions. In other examples, the protease is inactivated, e.g., by heat treatment, or removed (e.g., by a size exclusion purification step that removes protease as well as free polymerases, by affinity purification through binding to an affinity tag on the protease, or the like).

In further examples, loading compositions containing free polymerases and polymerase enzyme complexes are enriched for the polymerase enzyme complexes, and the polymerase enzyme complexes are maintained in an inactive form (e.g., the polymerases are not actively synthesizing nucleic acids even if bound to a template nucleic acid through association with a replication initiating moiety such as a primer). The enrichment can be accomplished using any of the methods described herein, including protease treatment, size exclusion purification, or a combination thereof. The polymerase enzyme complexes are in particular instances maintained in an inactive form by maintaining a concentration of one or more non-catalytic metal ions in the loading composition and/or on the substrate if the loading composition has been distributed onto a substrate. One or more nucleotides or nucleotide analogs (including, e.g., a mixture of nucleotides and nucleotide analogs) is typically also provided in the loading composition. In other instances, the polymerase enzyme complexes are maintained in an inactive form by maintaining a concentration of one or more non-hydrolyzable nucleotide analogs in the loading composition and/or on the substrate if the loading composition has been distributed onto a substrate. In some instances, the polymerase enzyme complexes are maintained in an inactive form by maintaining a concentration of one or more non-catalytic metal ions and of one or more non-hydrolyzable nucleotide analogs in the loading composition and/or on the substrate.

The above aspects and further exemplary embodiments are described in further detail in the following discussion.

II. Methods of Enriching Loading Compositions for Polymerase Enzyme Complexes Over Free Polymerases In general, methods disclosed herein enrich compositions for polymerase enzyme complexes by removing free polymerases from the composition. These compositions are in many aspects loading compositions that are used to deliver their components (including polymerase enzyme complexes) to a substrate.

The following sections describe embodiments of methods for enriching loading compositions for polymerase enzyme complexes. Although the following descriptions are for the sake of clarity described separately, it will be appreciated that any combination of the methods described herein in any order are encompassed by the invention disclosed herein. In addition, other methods of purification known in the art, including bead purification, can be used in combination with any of the methods described herein.

IIA. Protease Treatment

In certain aspects, enrichment for polymerase enzyme complexes in loading compositions is accomplished by applying a protease to the loading composition to remove the free polymerases. Without being bound to a particular mechanism of action, one potential reason for the differential effect of the protease on free polymerases versus polymerases that are part of complexes is that free polymerases are in a more open structural configuration that allows access for the degradative effects of the protease. In contrast, polymerases that are complexed with nucleic acids tend to be in a more closed tightly bound form that is able to resist protease digestion. This difference in the activity of protease on free versus complexed polymerases provides the ability to add excess polymerase to a primed DNA sample and then treat the sample with limited proteolytic digestion to remove any free, excess polymerase enzymes. Thus, the workflow of producing a loading composition of use in later analytical reactions (such as sequencing reactions) can be made more efficient and accurate by allowing for the formation of polymerase enzyme complexes and the removal of the free polymerases that may interfere with those later analytical reactions.

Proteases of use in the methods disclosed herein include without limitation endopeptidases, including for example trypsin, proteinase K, chymotrypsin, pepsin, papain, thermolysin, and elastase. The identity of the protease used in methods disclosed herein can depend on a number of factors, but in general the protease chosen is one that is effective against free polymerases but less (or not at all) effective against polymerases that are part of complexes with at least a template nucleic acid and also optionally with a replication initiating moiety. Complexes optionally also include a cognate nucleotide or nucleotide analog and/or a divalent metal ion (e.g., a non-catalytic or catalytic metal ion, as detailed below). General descriptions of stability and ligand binding effects on proteolytic susceptibility can be found for example in Park & Marqusee, Current Protocols in Protein Science (2006) 20.11.1-20.11.14 and Park & Marqusee, J. Mol. Biol. (2004) 343, 1467-1476.

In further embodiments, the protease is chosen based on structural components of the polymerase enzyme complex, particularly on components that assist in immobilizing the complex to a surface. In certain embodiments, the polymerase enzyme complex (and in particular embodiments, the polymerase of the complex) has as part of its structure a reactive element, and the complex can be immobilized to a surface through an interaction of the reactive element and a binding site on the substrate. In certain embodiments, the reactive element comprises streptavidin and the binding site comprises biotin. For example, a biotin-tagged polymerase can be bound to streptavidin; the streptavidin can serve as a reactive element for immobilization of the polymerase on a biotinylated substrate surface. In still further embodiments, the reactive element is resistant to cleavage by the protease. For example, if the reactive element (or a linker between the polymerase and the reactive element, e.g., a linker between a polymerase and a biotin tag that is bound to streptavidin) includes a peptide that contains no recognition sites for a particular protease, then that particular protease would be an effective choice for methods disclosed herein, particularly in embodiments in which the protease enrichment occurs after the loading composition is disposed on a substrate. In such embodiments, the added protease would only act upon the free polymerases on the surface of the substrate, but would not cleave the immobilized complexes from the substrate, allowing any subsequent reactions to occur on the substrate with the immobilized complexes intact.

The protease is generally applied as part of a buffer or any other solution that is compatible with other components of the loading composition. Suitable reaction conditions, including solution conditions and temperature, for various proteases are known in the art. As will be appreciated, the concentration of protease used will depend on the identity of the protease chosen. In certain embodiments, about 0.2-100 µg/ml, 0.5-50 µg/ml, 0.5-25 µg/ml, or 0.5-20 µg/ml of protease is used to remove free polymerases. In further embodiments, about 1-18, 2-16, 3-14, 4-12, 5-10, 6-8, 10-25, or 15-25 µg/ml of protease is used. Optionally at least 100 µg/ml, 250 µg/ml, 500 µg/ml, 1 mg/ml, or 5 mg/ml of protease is used.

In further embodiments, the protease is applied for a given length of time to remove free polymerases with minimal effect on other components of the loading composition. In still further embodiments, the protease is applied for at least 1, 2, 5, 10, 15, 20, 30, or 60 minutes, or even for at least 2, 4, 6, 8, or 10 hours. In yet further embodiments, the protease is applied for about 2-30, 5-28, 5-15, 10-26, 15-24, 20-22 minutes.

In certain embodiments, the protease is added to the loading composition prior to addition of the loading composition to any type of substrate—in other words, the protease is added in the bulk loading composition, which is in some situations a solution, prior to distribution of that loading composition onto a surface. In other embodiments, the loading composition is first added to a substrate and then the protease is also added to the substrate to remove free polymerases on the surface.

In further aspects, the protease treatment, whether provided before or after the loading composition is distributed onto a substrate, improves the accuracy of any subsequent sequencing reactions by about, or at least by about, 1%, 2%, 4%, 6%, 8%, 10%, 15%, 20%, 25%, 30%, 35%, 45% or 50% as compared to sequencing reactions that were conducted without a prior treatment of the loading composition with protease. In further embodiments, the protease treatment improves the accuracy of any subsequent sequencing reactions by about 1-10, 2-15, 3-20, 4-25, 5-30, 6-35, 7-40, 8-45, 9-50, or 10-55% as compared to sequencing reactions that were conducted without a prior treatment of the loading composition with protease.

In certain aspects and as is described in further detail herein, the loading composition includes without limitation polymerase enzyme complexes, free polymerases, at least one non-catalytic metal ion, and one or more nucleotides or nucleotide analogs. "Non-catalytic metal ions" as used herein refer to ions that interact with the polymerase, but that do not promote the polymerization reaction, and in many cases act to arrest or prevent polymerization. Such metal ions include for example strontium, cobalt, tin, calcium, nickel, europium, barium, iron, and zinc. In some embodiments, these metal ions are included in the loading composition in salt form, such as $Sr(OAc)_2$, $CoCl_2$, $SnCl_2$, $CaCl_2$, or $ZnSO_4$.

In further aspects, the polymerase enzyme complexes include a polymerase associated with a nucleic acid template and optionally further include a replication initiating moiety, including a standard oligonucleotide primer, or, alternatively, a component of the template, e.g., the template can be a self-priming single stranded DNA, a nicked double stranded DNA, or the like, or a terminal protein.

In specific embodiments, the loading composition includes polymerase enzyme complexes, free polymerases, strontium, and one or more nucleotides or nucleotide analogs. In further specific embodiments, the polymerase enzyme complexes comprise a polymerase complexed with a template nucleic acid through association with a primer that is itself hybridized to the template nucleic acid.

In further embodiments, the protease enrichment methods include multiple applications with the same or different protease, and in still further embodiments, such multiple protease applications can be accomplished in combination with other purification methods, such as size exclusion purification.

In certain examples, after treatment with a protease (with or without a size exclusion purification step), a protease inhibitor is added to the loading composition (or to the substrate if the loading composition has been distributed on a substrate). The protease inhibitor will halt the activity of the protease or otherwise inactivate the protease to prevent further degradation of components of the loading composition. Use of a protease inhibitor may also prevent interference with any subsequent reactions with the components of the loading composition—for example, any subsequent sequencing reactions.

Protease inhibitors that can be added to inactivate protease activity after free polymerases are sufficiently removed include any inhibitors known in the art. For example, PMSF (phenylmethylsulfonyl fluoride) is an effective inhibitor of serine proteases. There are in addition small molecule non covalent inhibitors, such as benzamidine. For trypsin in particular, there are also protein based noncovalent inhibitors, such as basic pancreatic trypsin inhibitor, which has a very tight binding constant for trypsin. Covalent inhibitors of trypsin include serpins (serine protease inhibitors). The choice of protease inhibitor to include will depend on the protease used as well as on other factors, including interactions with other components of the loading composition, or any other subsequent compositions added (such as sequencing reaction mixtures), pH sensitivity, isoelectric point, and concentrations required for effective inhibition.

In further embodiments, the polymerase enzyme complexes are maintained in an inactive form during enrichment and purification steps—in other words, the polymerases are not actively synthesizing nucleic acids even if bound to a template nucleic acid through association with a replication initiating moiety such as a primer. The polymerase enzyme complexes are in particular instances maintained in the inactive form by including a concentration of one or more non-catalytic metal ions in the loading composition and/or on the substrate if the loading composition has been distributed onto a substrate. As discussed above, such non-catalytic metal ions can include strontium, cobalt, tin, calcium, nickel, europium, barium, iron, and zinc. Including one or more cognate nucleotides or nucleotide analogs (e.g., a mixture of dATP, dCTP, dGTP, and dTTP) in the loading composition and/or on the substrate can assist in maintaining stability of the complex. In other instances, the polymerase enzyme complexes are maintained in the inactive form by including a concentration of one or more non-hydrolyzable nucleotide analogs in the loading composition and/or on the substrate if the loading composition has been distributed onto a substrate. Suitable non-hydrolyzable nucleotide analogs are known in the art and include, e.g., analogs with, e.g., an amino, methyl, thio, or other linkage not hydrolyzed by polymerase activity between the alpha and beta phosphates. Optionally, the polymerase enzyme complexes are maintained in the inactive form by including a concentration of one or more non-catalytic metal ions and of one or more non-hydrolyzable nucleotide analogs in the loading composition and/or on the substrate.

In certain non-limiting embodiments, prior to or following protease treatment, the loading composition is distributed to a substrate. In certain embodiments, the substrate to which the polymerase compositions are distributed can further include a plurality of array regions, which may in turn comprise nanowells. Those nanowells may comprise without limitation zero mode waveguides (ZMWs). In some embodiments, the substrate to which the polymerase compositions are distributed following protease treatment can have surfaces with a circular geometry or a rectangular geometry. Such a surface may further comprise about 120,000 to about 5,000,000 nanoscale wells such as ZMWs, e.g., about 120,000 to about 2,000,000 nanoscale wells. In embodiments in which the surface has a circular geometry, the surface in general comprises about 100,000; 150,000; 200,000; 250,000 ZMWs. In embodiments in which the surface has a rectangular geometry, the surface comprises about 750,000; 1,000,000; 1,500,000; 2,000,000; 3,000,000; 4,000,000; 5,000,000 ZMWs. Optionally, the surface comprises between 400,000 and 20,000,000 ZMWs, e.g., between 1,000,000 and 16,000,000 ZMWs, e.g., 1,000,000, 2,000,000, 3,000,000, 4,000,000, 5,000,000, 6,000,000, 7,000,000, 8,000,000, 9,000,000, or 10,000,000 ZMWs. Further details on substrates are provided in later sections herein. Optionally, the polymerase enzyme complexes are immobilized to the substrate, for example, to the bottom surface of nanoscale wells.

II.B. Other Purification Methods

In some aspects, other purification methods are used to isolate free polymerases from the loading composition in order to enrich the loading composition for polymerase enzyme complexes. These purification methods may be used alone or in addition to the protease enrichment methods discussed above.

In one embodiment, a size exclusion method is used to separate free polymerase from the desired polymerase enzyme complexes. Such a size exclusion method can use any method used in the art, including size exclusion spin columns utilizing gel filtration media, including Sephacryl columns such as the GE S400. In embodiments in which the polymerase enzyme complexes are maintained in an inactive form through presence of a non-catalytic metal ion and nucleotides (or of non-hydrolyzable nucleotide analogs), these components are desirably also present in the buffer with which the gel filtration column is pre-equilibrated before application of the loading composition to the column. Filtered loading compositions can be used right away in further enrichment methods or for downstream applications such as sequencing applications. Filtered loading compositions may also be stored, e.g., at 4° C., for periods of time and still be used effectively for downstream applications. In certain embodiments, such filtered loading compositions can be stored for 6-56, 12-48, 18-40, 24-34 hours at 4° C.

Further examples of size-based purification methods include size exclusion chromatography, gel filtration chromatography, and gel permeation chromatography.

Other purification methods that can be used include gel electrophoresis, extraction, precipitation, ultracentrifugation, ion exchange chromatography, affinity chromatography and HPLC.

In some embodiments, isolated active polymerase enzyme complexes are isolated using an affinity column. For example, it is known that a nucleotide mimic affinity column can be used to purify a polymerase enzyme. See, e.g. Sotirios et al. Biotechnol. J., 2, 121-132, 2007. In certain methods, a nucleotide is attached to the resin in a column through its polyphosphate portion to produce a nucleotide-phosphate affinity column. This column can be used to isolate active polymerase enzyme-template complexes from inactive complexes and other components in the solution. Such method are described for example in U.S. Pat. No. 8,936,911 which is hereby incorporated by reference in its entirety for all purposes and in particular for all teachings related to isolating polymerase enzyme complexes.

In some embodiments, free polymerases are removed by applying particles to the loading composition. In some embodiments, the particle is a paramagnetic particle that captures free polymerases and polymerases that are bound to primers but are not otherwise part of polymerase-template complexes. In further embodiments, a plurality of oligonucleotides are attached to the paramagnetic particles, and in yet further embodiments, the molecules that are to be removed attach to the oligonucleotides, and the cleaning step further comprises removing the particles and their attached molecules. The attachment of the molecules to be removed can include binding, hybridization, or any other association with the oligonucleotides. Further details on such particle based methods are described for example in co-pending application U.S. Provisional Application No. 62/257,152, filed on Nov. 18, 2015, which is hereby incorporated by reference in its entirety for all purposes and in particular for all teachings related to isolating polymerase enzyme complexes.

II.C. Combinations

As discussed above, any of the enrichment methods described herein can be conducted in any combination.

In specific embodiments, a protease treatment and a size exclusion purification are conducted on the bulk loading composition—e.g., in solution prior to addition of the loading composition to a substrate or other platform for subsequent analyses. In some embodiments, the protease treatment occurs prior to the size exclusion purification, whereas in other embodiments, the protease treatment occurs after the size exclusion purification.

In further embodiments, a protease treatment step takes place after the loading composition is distributed on a substrate or any other platform. In certain embodiments, a size exclusion purification step takes place prior to the loading composition being distributed on the substrate.

In further embodiments one or more different purification steps are repeated one or more times in any combination. For example, a protease treatment step can be followed by a size exclusion purification step which can then be followed by a second protease treatment step, e.g., with a loading step between the size exclusion step and the second protease step. As will be appreciated, any combination of any number of repetitions of different enrichment method steps is encompassed by the present disclosure.

Protease enrichment steps and/or size exclusion purifications may further be combined with other enrichment methods, including without limitation magnetic bead capture, affinity purification, chemical degradation methods, molecular sieve, gel filtration, and the like.

In certain embodiments, the purification methods are further enhanced by use of one or more agents that stabilize the complex during purification. There are certain sets of conditions that tend to favor the stability of the enzyme-template complex. For example, the addition of a stabilizing divalent metal such as $Ca^{2+}$, $Sr^{2+}$, $Ba^{2+}$, $Ti^{2+}$, $Ni^{2+}$, $Co^{2+}$, $Sn^{2+}$, $Eu^{2+}$, $Fe^{2+}$, or $Zn^{2+}$ can provide enhanced stability of the polymerase enzyme complex during purification. The divalent metal ions can be removed before using the polymerase complex in an analysis reaction such as sequencing, although in some embodiments the addition of $Ca^{2+}$ or another non-catalytic ion is advantageous. Note that these metals have the advantage that they can also be used to halt the polymerase reaction as described above, and be retained during purification to provide stability. While not being bound by theory, it is believed that the stabilizing cation acts to stabilize the ternary complex, for example by stabilizing the incoming nucleotide's interaction with the polymerase and template DNA. See, for example, Franklin, et al., Cell, Vol. 105, 657-667, 2001. In some cases, the presence of one or more nucleotides will enhance the stability of the polymerase-template complex. Nucleotides added for stabilization can be incorporable or non-incorporable nucleotides. They can be natural nucleotides, or nucleotide analogs. The nucleotide analogs generally have added groups not present in the natural nucleotides, but nonetheless are optionally able to be incorporated by a polymerase enzyme. In some cases, the nucleotide or analog added to improve stability will be the same type of nucleotide or analog that is used during the analysis reaction. In other cases, different nucleotides or analogs are employed. For example, a mixture of the four standard dNTPs can be added to improve stability during enrichment and/or purification, while one or more (e.g., two, three, or four) fluorescently labeled nucleotide analogs generating different signals are employed during analysis, e.g., sequencing. As another example, one or more non-hydrolyzable (and therefore also non-incorporable) nucleotide analogs (e.g., analogs with an amino, methyl, thio, or other linkage not hydrolyzed by polymerase activity between the alpha and beta phosphates) can be added to improve stability during enrichment and/or purification, while one or more (e.g., two, three, or four) fluorescently labeled nucleotide analogs generating different signals are employed during analysis, e.g., sequencing. Nucleotide analogs, including analogs useful in sequencing, are described below and are well known in the art. Other additives can be included in order to further stabilize the composition including glycerol, betaine, polyethylene glycol and surface active agents such as Tween20.

III. Compositions

IIIA. Template Molecules

Any of the methods and complexes described herein can include template nucleic acid molecules (also referred to herein as "template sequences"), often as part of the polymerase enzyme complexes described herein. In general, the template nucleic acid is the molecule for which the complementary sequence is synthesized in the polymerase reaction. In some cases, the template nucleic acid is linear; in some cases, the template nucleic acid is circular. The template nucleic acid can be DNA, RNA, or can be a non-natural RNA analog or DNA analog. Any template nucleic acid that is suitable for replication by a polymerase enzyme can be used in the methods and systems described herein.

In some embodiments, the template nucleic acids used in methods and compositions of the present invention comprise nucleic acids obtained from a sample. The sample may comprise any number of things, including, but not limited to, bodily fluids (including, but not limited to, blood, urine, serum, lymph, saliva, anal and vaginal secretions, perspiration and semen) and cells of virtually any organism, with mammalian samples being preferred and human samples being particularly preferred; environmental samples (including, but not limited to, air, agricultural, water and soil samples); biological warfare agent samples; research samples (i.e. in the case of nucleic acids, the sample may be the products of an amplification reaction, including both target and signal amplification, such as PCR amplification reactions; purified samples, such as purified genomic DNA, RNA preparations, raw samples (bacteria, virus, genomic DNA, etc.); as will be appreciated by those in the art, virtually any experimental manipulation may have been done on the samples.

In further embodiments, nucleic acid molecules are obtained from a sample and fragmented for use in methods of the invention as template nucleic acids. The fragments may be single or double stranded and may further be modified in accordance with any methods known in the art and described herein. Template nucleic acids may be generated by fragmenting source nucleic acids, such as genomic DNA, using any method known in the art. In one embodiment, shear forces during lysis and extraction of genomic DNA generate fragments in a desired range. Also encompassed by the invention are methods of fragmentation utilizing restriction endonucleases.

As will be appreciated, the template nucleic acids may be generated from a source nucleic acid, such as genomic DNA, by fragmentation to produce fragments of a specific size. The target nucleic acids can be, for example, from about 10 to about 100,000 nucleotides in length, from about 10 to about 50,000 nucleotides in length, or from about 10 to about 20,000 nucleotides in length. In one embodiment, the fragments are 50 to 600 nucleotides in length. In another embodiment, the fragments are 300 to 600 or 200 to 2000 nucleotides in length. In yet another embodiment, the fragments are 10-100, 50-100, 50-300, 100-200, 200-300, 50-400, 100-400, 200-400, 400-500, 400-600, 500-600, 50-1000, 100-1000, 200-1000, 300-1000, 400-1000, 500-1000, 600-1000, 700-1000, 700-900, 700-800, 800-1000, 900-1000, 1500-2000, 1750-2000, and 50-2000 nucleotides in length. In yet further embodiments, the nucleic acid templates are 10-100, 50-100, 50-300, 100-200, 200-300, 50-400, 100-400, 200-400, 400-500, 400-600, 500-600, 50-1000, 100-1000, 200-1000, 300-1000, 400-1000, 500-1000, 600-1000, 700-1000, 700-900, 700-800, 800-1000, 900-1000, 1500-2000, 1750-2000, 50-2000, 100-25000, 200-24000, 300-23000, 400-22000, 500-21000, 600-20000, 700-19000, 800-18000, 900-17000, 1000-16000, 1100-15000, 1200-14000, 1300-13000, 1400-12000, 1500-11000, 1600-10000, 1700-9000, 1800-8000, 1900-7000, 2000-6000, 2100-5000, 2200-4000, 2300-3000, 10000-30000, 12000-28000, 14000-26000, 16000-24000, 18000-22000, 19000-20000, 20000-40000, or 40000-60000 nucleotides in length. In further embodiments, the nucleic acid templates are part of polymerase-template complexes. In yet further embodiments, the nucleic acid templates are themselves further hybridized to primers.

In some cases, the template sequence may be a linear single or double stranded nucleic acid sequence. In still other embodiments, the template may be provided as a circular or functionally circular construct that allows redundant processing of the same nucleic acid sequence by the synthesis complex. Use of such circular constructs has been described in, e.g., U.S. Pat. No. 7,315,019 and U.S. patent application Ser. No. 12/220,674, filed Jul. 25, 2008, and alternate functional circular constructs are also described in US Pat. App. Pub. No. 20090298075, the full disclosures of each of which are incorporated herein by reference in their entirety for all purposes and in particular for all teachings related to template nucleic acid constructs. Briefly, such alternate constructs include template sequences that possess a central double stranded portion that is linked at each end by an appropriate linking oligonucleotide, such as a hairpin loop segment. Such structures not only provide the ability to repeatedly replicate a single molecule (and thus sequence that molecule), but also provide for additional redundancy by replicating both the sense and antisense portions of the double stranded portion. In the context of sequencing applications, such redundant sequencing provides great advantages in terms of sequence accuracy.

In further aspects, the template nucleic acid used in the compositions of the present invention includes: a double stranded nucleic acid segment having a first and second end; a first hairpin oligonucleotide connecting each strand of the single template nucleic acid at the first end; a second hairpin oligonucleotide connecting each strand of the single template nucleic acid at the second end. In some embodiments, the first hairpin and second hairpin oligonucleotide are identical. In other embodiments, the first hairpin and second hairpin oligonucleotides are not identical—in other words, the template nucleic acid, despite being an alternate circular construct, is nevertheless asymmetrical. In further embodiments, the first hairpin oligonucleotide includes a primer binding site whereas the second hairpin oligonucleotide includes a capture adapter (or vice versa). The capture adapter is generally of a sequence that can be used to enrich a population for the hairpins of choice—for example, in some embodiments, the capture adapter comprises a polyA sequence, thereby allowing capture using beads or column chromatography utilizing polyT sequences. In other embodiments, the capture adapter comprises at least one methoxy residue. In further embodiments, the capture adapter is complementary to an oligonucleotide attached to a bead, which can in further embodiments be a magnetic bead that can be used to enrich a population for template nucleic acids containing the capture adapter. In some embodiments in which the population of templates includes templates with different adapters or in which each template comprises a different adapter at each end, different beads can be used which contain oligonucleotides complementary to the different adapters. Thus, for templates with two different adapters, two different beads can be used. For populations containing a plurality of different adapters, a concomitant number of different types of beads can be used that are directed to those adapters. In other embodiments, the same bead can contain different oligonucleotides complementary to the different adapters in the population of templates, such that the same bead can capture different adapters (and their associated templates).

In still further embodiments, the first or second hairpin comprises a self-primed adapter sequence in which the primer is part of the adapter. In such embodiments, an additional oligonucleotide primer is not needed to allow a polymerase molecule to begin replicating the template.

In yet further embodiments, the nucleic acid template contains only a single hairpin at one end or the other.

III.B. Nucleotides and Nucleotide Analogs

Nucleotides of use in the present invention include, e.g., naturally occurring nucleotides such as dATP, dCTP, dGTP, and dTTP. Various nucleotide analogs are also of use in the present invention. For example, non-hydrolyzable analogs can be employed to maintain a polymerase complex in an inactive form, and labelled incorporable analogs can be employed during nucleic acid sequencing. Upon incorporation into a growing oligonucleotide chain, the analog can leave a residue that is the same as or different than a natural nucleotide in the growing oligonucleotide (the polymerase can incorporate any non-standard moiety of the analog, or can cleave it off during incorporation into the oligonucleotide). A "nucleotide analog" herein is a compound, that, in a particular application, functions in a manner similar or analogous to a naturally occurring nucleoside triphosphate (a "nucleotide"), and does not otherwise denote any particular structure. A nucleotide analog is an analog other than a standard naturally occurring nucleotide, i.e., other than A, G, C, T, or U, though upon incorporation into the oligonucleotide, the resulting residue in the oligonucleotide can be the same as (or different from) an A, G, C, T, or U residue.

In one useful aspect of the invention, nucleotide analogs can be modified to enhance complex stabilization or sequencing properties. For example, various linkers or other substituents can be incorporated into analogs that have the effect of reducing branching fraction, improving processivity, or altering rates. Modifications to the analogs can include extending the phosphate chains, e.g., to include a tetra-, penta-, hexa- or heptaphosphate group, and/or adding chemical linkers to extend the distance between the nucleotide base and the dye molecule, e.g., a fluorescent dye molecule. Substitution of one or more non-bridging oxygen in the polyphosphate, for example with S or $BH_3$, can change the polymerase reaction kinetics, e.g., to achieve a system having two slow steps as described hereinbelow. Optionally, one or more, two or more, three or more, four or more non-bridging oxygen atoms in the polyphosphate group of the analog has an S substituted for an O. While not being bound by theory, it is believed that the properties of the nucleotide, such as the metal chelation properties, electronegativity, or steric properties, can be altered by substitution of the non-bridging oxygen(s).

Many nucleotide analogs are available and can be incorporated by polymerases. These include analog structures with core similarity to naturally occurring nucleotides, such as those that comprise one or more substituent on a phosphate, sugar, or base moiety of the nucleoside or nucleotide relative to a naturally occurring nucleoside or nucleotide. In one embodiment, the nucleotide analog includes three phosphate containing groups; for example, the analog can be a labeled nucleoside triphosphate analog and/or an α-thiophosphate nucleotide analog having three phosphate groups. In one embodiment, a nucleotide analog can include one or more extra phosphate containing groups, relative to a nucleoside triphosphate. For example, a variety of nucleotide analogs that comprise, e.g., from 4-6 or more phosphates are described in detail in US patent application publication 2007-0072196, incorporated herein by reference in its entirety for all purposes. Other exemplary useful analogs, including tetraphosphate and pentaphosphate analogs, are described in U.S. Pat. No. 7,041,812, incorporated herein by reference in its entirety for all purposes.

For example, the analog can include a labeled compound of the formula:

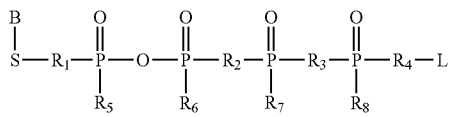

wherein B is a nucleobase (and optionally includes a label); S is selected from a sugar moiety, an acyclic moiety or a carbocyclic moiety (and optionally includes a label); L is an optional detectable label; $R_1$ is selected from O and S; $R_2$, $R_3$ and $R_4$ are independently selected from O, NH, S, methylene, substituted methylene, C(O), $C(CH_2)$, $CNH_2$, $CH_2CH_2$, and $C(OH)CH_2R$ where R is 4-pyridine or 1-imidazole, provided that $R_4$ may additionally be selected from

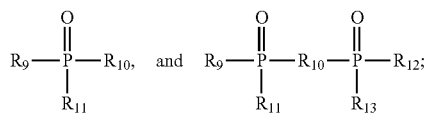

$R_5$, $R_6$, $R_7$, $R_8$, $R_{11}$ and $R_{13}$ are, when present, each independently selected from O, $BH_3$, and S; and $R_9$, $R_{10}$ and $R_{12}$ are independently selected from O, NH, S, methylene, substituted methylene, $CNH_2$, $CH_2CH_2$, and $C(OH)CH_2R$ where R is 4-pyridine or 1-imidazole. In some cases, phosphonate analogs may be employed as the analogs, e.g., where one of $R_2$, $R_3$, $R_4$, $R_9$, $R_{10}$ or $R_{12}$ are not O, e.g., they are methyl etc. See, e.g., US patent application publication 2007-0072196, previously incorporated herein by reference in its entirety for all purposes.

The base moiety incorporated into the analog is generally selected from any of the natural or non-natural nucleobases or nucleobase analogs, including, e.g., purine or pyrimidine bases that are routinely found in nucleic acids and available nucleic acid analogs, including adenine, thymine, guanine, cytosine, uracil, and in some cases, inosine. As noted, the base optionally includes a label moiety. For convenience, nucleotides and nucleotide analogs are generally referred to based upon their relative analogy to naturally occurring nucleotides. As such, an analog that operates, functionally, like adenosine triphosphate, may be generally referred to herein by the shorthand letter A. Likewise, the standard abbreviations of T, G, C, U and I, may be used in referring to analogs of naturally occurring nucleosides and nucleotides typically abbreviated in the same fashion. In some cases, a base may function in a more universal fashion, e.g., functioning like any of the purine bases in being able to hybridize with any pyrimidine base, or vice versa. The base moieties used in the present invention may include the conventional bases described herein or they may include such bases substituted at one or more side groups, or other fluorescent bases or base analogs, such as 1,N6 ethenoadenosine or pyrrolo C, in which an additional ring structure renders the B group neither a purine nor a pyrimidine. For example, in certain cases, it may be desirable to substitute one or more side groups of the base moiety with a labeling group or a component of a labeling group, such as one of a donor or acceptor fluorophore, or other labeling group. Examples of labeled nucleobases and processes for labeling such groups are described in, e.g., U.S. Pat. Nos. 5,328,824 and 5,476,928, each of which is incorporated herein by reference in its entirety for all purposes.

In the analogs, the S group is optionally a sugar moiety that provides a suitable backbone for a synthesizing nucleic acid strand. For example, the sugar moiety is optionally selected from a D-ribosyl, 2' or 3' D-deoxyribosyl, 2',3'-D-dideoxyribosyl, 2', 3'-D-didehydrodideoxyribosyl, 2' or 3' alkoxyribosyl, 2' or 3' aminoribosyl, 2' or 3' mercaptoribosyl, 2' or 3' alkothioribosyl, acyclic, carbocyclic or other modified sugar moieties. A variety of carbocyclic or acyclic moieties can be incorporated as the "S" group in place of a sugar moiety, including, e.g., those described in U.S. Patent Application Publication No. 2003/0124576, which is incorporated herein by reference in its entirety for all purposes.

For most cases, the phosphorus containing chain in the analogs, e.g., a triphosphate in conventional NTPs, is preferably coupled to the 5' hydroxyl group, as in natural nucleoside triphosphates. However, in some cases, the phosphorus containing chain is linked to the S group by the 3' hydroxyl group.

L generally refers to a detectable labeling group that is coupled to the terminal phosphorus atom via the $R_4$ (or $R_{10}$ or $R_{12}$ etc.) group. The labeling groups employed in the analogs of the invention may comprise any of a variety of detectable labels. Detectable labels generally denote a chemical moiety that provides a basis for detection of the analog compound separate and apart from the same compound lacking such a labeling group. Examples of labels include, e.g., optical labels, e.g., labels that impart a detectable optical property to the analog, electrochemical labels, e.g., labels that impart a detectable electrical or electrochemical property to the analog, and physical labels, e.g., labels that impart a different physical or spatial property to the analog, e.g., a mass tag or molecular volume tag. In some cases individual labels or combinations may be used that impart more than one of the aforementioned properties to the analogs of the invention.

Optionally, the labeling groups incorporated into the analogs comprise optically detectable moieties, such as luminescent, chemiluminescent, fluorescent, fluorogenic, chromophoric and/or chromogenic moieties, with fluorescent and/or fluorogenic labels being preferred. A variety of different label moieties are readily employed in nucleotide analogs. Such groups include, e.g., fluorescein labels, rhodamine labels, cyanine labels (i.e., Cy3, Cy5, and the like, generally available from the Amersham Biosciences division of GE Healthcare), and the Alexa family of fluorescent dyes and other fluorescent and fluorogenic dyes available from Molecular Probes/Invitrogen, Inc. and described in The Handbook—A Guide to Fluorescent Probes and Labeling Technologies, Eleventh Edition' (2010) (available from Invitrogen, Inc./Molecular Probes). A variety of other fluorescent and fluorogenic labels for use with nucleoside polyphosphates, and which would be applicable to the nucleotide analogs incorporated by the polymerases of the present invention, are described in, e.g., U.S. Patent Application Publication No. 2003/0124576, previously incorporated herein by reference in its entirety for all purposes.

Thus, in one illustrative example, the analog can be a phosphate analog (e.g., an analog that has more than the typical number of phosphates found in nucleoside triphosphates) that includes, e.g., an Alexa dye label. For example, an Alexa488 dye can be labeled on a delta phosphate of a tetraphosphate analog (denoted, e.g., A488dC4P or A488dA4P, for the Alexa488 labeled tetraphosphate analogs of C and A, respectively), or an Alexa568 or Alexa633 dye can be used (e.g., A568dC4P and A633dC4P, respectively, for labeled tetraphosphate analogs of C or A568dT6P for a labeled hexaphosphate analog of T), or an Alexa546 dye can be used (e.g., A546dG4P), or an Alexa594 dye can be used (e.g., A594dT4P). As additional examples, an Alexa555 dye (e.g., A555dC6P or A555dA6P), an Alexa 647 dye (e.g., A647dG6P), an Alexa 568 dye (e.g., A568dT6P), and/or an Alexa660 dye (e.g., A660dA6P or A660dC6P) can be used in, e.g., single molecule sequencing. Similarly, to facilitate color separation, a pair of fluorophores exhibiting FRET (fluorescence resonance energy transfer) can be labeled on a delta phosphate of a tetraphosphate analog (denoted, e.g., FAM-amb-A532dG4P or FAM-amb-A594dT4P).

As noted above, an analog can include a linker that extends the distance between the nucleotide base and the label moiety, e.g., a fluorescent dye moiety. Exemplary linkers and analogs are described in U.S. Pat. No. 7,968,702. Similarly, a protein or other moiety can be employed to provide spacing and/or shielding between the base and the label, e.g., as described in U.S. patent application Ser. No. 13/767,619 "Polymerase Enzyme Substrates with Protein Shield" filed Feb. 14, 2013, and U.S. patent application Ser. No. 14/452,497 "Protected Fluorescent Reagent Compounds" filed Aug. 5, 2013. Suitable polymerase substrates optionally include two or more nucleoside polyphosphates and/or two or more label moieties, e.g., as described in U.S. patent application Ser. No. 13/767,619 "Polymerase Enzyme Substrates with Protein Shield," U.S. patent application Ser. No. 14/452,497 "Protected Fluorescent Reagent Compounds," and US patent application publication 2009-0208957 Alternate Labeling Strategies for Single Molecule Sequencing.

Additional details regarding labels, analogs, and methods of making such analogs can be found in US patent application publication 2007-0072196, WO 2007/041342 Labeled Nucleotide Analogs and Uses Therefor, WO 2009/114182 Labeled Reactants and Their Uses, US patent application publication 2009-0208957 Alternate Labelling Strategies for Single Molecule Sequencing, U.S. patent application Ser. No. 13/218,412 Functionalized Cyanine Dyes, U.S. patent application Ser. No. 13/218,395 Functionalized Cyanine Dyes, U.S. patent application Ser. No. 13/218,428 Cyanine Dyes, U.S. patent application Ser. No. 13/218,382 Scaffold-Based Polymerase Enzyme Substrates, US patent application publication 2010-0167299 Phospholink Nucleotides for Sequencing Applications, US patent application publication 2010-0152424 Modular Nucleotide Compositions and Uses Therefor, U.S. patent application Ser. No. 13/767,619 "Polymerase Enzyme Substrates with Protein Shield," and U.S. patent application Ser. No. 14/452,497 "Protected Fluorescent Reagent Compounds," each of which is incorporated herein by reference in its entirety for all purposes.

III.C. Polymerases

The methods and compositions of the present disclosure utilize polymerase enzymes (also referred to herein as "polymerases"). Any suitable polymerase enzyme can be used in the systems and methods disclosed herein. Suitable polymerases include DNA dependent DNA polymerases, DNA dependent RNA polymerases, RNA dependent DNA polymerases (reverse transcriptases), and RNA dependent RNA polymerases. In certain embodiments, the polymerases used in the methods and compositions of the present invention are strand-displacing polymerases.

As disclosed in further detail herein, polymerases of use in the presently disclosed methods may include modifications that improve certain characteristics of the enzyme, including processivity, resistance to photodamage, and conduciveness to immobilization. In certain aspects, polymerases used in the methods and systems disclosed herein include a linker through which the polymerases (and any other molecules they are complexed with, such as template nucleic acids and optionally replication initiating moieties) can be immobilized onto a surface. In certain aspects, these linkers are resistant to cleavage by a protease. Such linkers can be designed in conjunction with choices made for protease treatment methods. For example, for the enrichment methods described herein that utilize the protease trypsin, polymerases of use in such methods can be designed to include linkers that are resistant to digestion by trypsin, e.g., peptide linkers that contain no lysine or arginine side chains, which are recognition sites for trypsin activity. Thus, complexes containing such enzymes (and their linkers) that are immobilized on the surface of a substrate can be treated with trypsin to remove free polymerases from the bulk solution around them without cleaving the enzyme complexes away from their location on the substrate. As will be appreciated, the nature of the linker can be designed to be of use (e.g., be resistant to) the protease used to remove free polymerases. For example, Proteinase K predominately cleaves proteins at the peptide bond adjacent to the carboxyl group of aliphatic and aromatic amino acids, and thus a linker lacking such amino acids would be used in methods utilizing this protease.

DNA polymerases are sometimes classified into six main groups based upon various phylogenetic relationships, e.g., with *E. coli* Pol I (class A), *E. coli* Pol II (class B), *E. coli* Pol III (class C), Euryarchaeotic Pol II (class D), human Pol beta (class X), and *E. coli* UmuC/DinB and eukaryotic RAD30/xeroderma pigmentosum variant (class Y). For a review of recent nomenclature, see, e.g., Burgers et al. (2001) "Eukaryotic DNA polymerases: proposal for a revised nomenclature" J Biol Chem. 276(47):43487-90. For a review of polymerases, see, e.g., HUbscher et al. (2002) "Eukaryotic DNA Polymerases" Annual Review of Biochemistry Vol. 71: 133-163; Alba (2001) "Protein Family Review: Replicative DNA Polymerases" Genome Biology 2(1):reviews 3002.1-3002.4; and Steitz (1999) "DNA polymerases: structural diversity and common mechanisms" J Biol Chem 274:17395-17398. The basic mechanisms of action for many polymerases have been determined. The sequences of literally hundreds of polymerases are publicly available, and the crystal structures for many of these have been determined, or can be inferred based upon similarity to solved crystal structures of homologous polymerases. For example, the crystal structure of φ29, a preferred type of parental enzyme to be modified according to the invention, is available.

In addition to wild-type polymerases, chimeric polymerases made from a mosaic of different sources can be used. For example, φ29 polymerases made by taking sequences from more than one parental polymerase into account can be used as a starting point for mutation to produce the polymerases of the invention. Chimeras can be produced, e.g., using consideration of similarity regions between the polymerases to define consensus sequences that are used in the chimera, or using gene shuffling technologies in which multiple φ29-related polymerases are randomly or semi-randomly shuffled via available gene shuffling techniques (e.g., via "family gene shuffling"; see Crameri et al. (1998) "DNA shuffling of a family of genes from diverse species accelerates directed evolution" Nature 391:288-291; Clackson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mol. Biol. 330:287-296). In these methods, the recombination points can be predetermined such that the gene fragments assemble in the correct order. However, the combinations, e.g., chimeras, can be formed at random. For example, using methods described in Clarkson et al., five gene chimeras, e.g., comprising segments of a Phi29 polymerase, a PZA polymerase, an M2 polymerase, a B103 polymerase, and a GA-1 polymerase, can be generated. Appropriate mutations to improve branching fraction, increase closed complex stability, or alter reaction rate constants can be introduced into the chimeras.

Available DNA polymerase enzymes have also been modified in any of a variety of ways, e.g., to reduce or eliminate exonuclease activities (many native DNA polymerases have a proof-reading exonuclease function that interferes with, e.g., sequencing applications), to simplify production by making protease digested enzyme fragments such as the Klenow fragment recombinant, etc. As noted, polymerases have also been modified to confer improvements in specificity, processivity, and improved retention time of labeled nucleotides in polymerase-DNA-nucleotide complexes (e.g., WO 2007/076057 Polymerases For Nucleotide Analogue Incorporation by Hanzel et al. and WO 2008/051530 Polymerase Enzymes And Reagents For Enhanced Nucleic Acid Sequencing by Rank et al.), to alter branch fraction and translocation (e.g., US Pub. No. 20100075332 entitled "Engineering Polymerases And Reaction Conditions For Modified Incorporation Properties"), to increase photostability (e.g., US Pub. No. 20100093555 entitled "Enzymes Resistant to Photodamage"), and to improve surface-immobilized enzyme activities (e.g., WO 2007/075987 Active Surface Coupled Polymerases by Hanzel et al. and WO 2007/076057 Protein Engineering Strategies To Optimize Activity Of Surface Attached Proteins by Hanzel et al.). Any of these available polymerases can be modified in accordance with the methods known in the art to decrease branching fraction formation, improve stability of the closed polymerase-DNA complex, and/or alter reaction rate constants. In some cases, the polymerase is modified in order to more effectively incorporate the nucleotide analogs of the invention, e.g. analogs having four or more phosphates in their polyphosphate chain. Enzymes mutated to more readily accept nucleotide analogs having such properties are described, for example in the applications described above and in US 20120034602—Recombinant Polymerases for Improved Single Molecule Sequencing; US 20100093555—Enzymes Resistant to Photodamage; US 20110189659—Generation of Modified Polymerases for Improved Accuracy in Single Molecule Sequencing; US 20100112645—Generation of Modified Polymerases for Improved Accuracy in Single Molecule Sequencing; US 2008/0108082—Polymerase enzymes and reagents for enhanced nucleic acid sequencing; and US 20110059505—Polymerases for Nucleotide Analogue Incorporation which are incorporated herein by reference in their entirety for all purposes.

Many polymerases that are suitable for modification are available, e.g., for use in sequencing, labeling and amplification technologies. For example, human DNA Polymerase Beta is available from R&D systems. DNA polymerase I is available from Epicenter, GE Health Care, Invitrogen, New England Biolabs, Promega, Roche Applied Science, Sigma Aldrich and many others. The Klenow fragment of DNA Polymerase I is available in both recombinant and protease digested versions, from, e.g., Ambion, Chimerx, eEnzyme LLC, GE Health Care, Invitrogen, New England Biolabs, Promega, Roche Applied Science, Sigma Aldrich and many others. φ29 DNA polymerase is available from e.g., Epicentre. Poly A polymerase, reverse transcriptase, Sequenase, SP6 DNA polymerase, T4 DNA polymerase, T7 DNA polymerase, and a variety of thermostable DNA polymerases (Taq, hot start, titanium Taq, etc.) are available from a variety of these and other sources. Recent commercial DNA polymerases include Phusion™ High-Fidelity DNA Polymerase, available from New England Biolabs; GoTaq® Flexi DNA Polymerase, available from Promega; RepliPHI™ Φ29 DNA Polymerase, available from Epicentre Biotechnologies; PfuUltra™ Hotstart DNA Polymerase, available from Stratagene; KOD HiFi DNA Polymerase, available from Novagen; and many others. Biocompare(dot)com provides comparisons of many different commercially available polymerases.

DNA polymerases that are preferred substrates for mutation to decrease branching fraction, increase closed complex stability, or alter reaction rate constants include Taq polymerases, exonuclease deficient Taq polymerases, *E. coli* DNA Polymerase 1, Klenow fragment, reverse transcriptases, Φ29-related polymerases including wild type Φ29 polymerase and derivatives of such polymerases such as exonuclease deficient forms, T7 DNA polymerase, T5 DNA polymerase, an RB69 polymerase, etc.

In one aspect, the polymerase of use in the methods and compositions described herein is a modified Φ29-type DNA polymerase. For example, the modified recombinant DNA polymerase can be homologous to a wild-type or exonuclease deficient Φ29 DNA polymerase, e.g., as described in U.S. Pat. Nos. 5,001,050, 5,198,543, or 5,576,204. Alternately, the modified recombinant DNA polymerase can be homologous to other Φ29-type DNA polymerases, such as B103, GA-1, PZA, Φ15, BS32, M2Y, Nf, G1, Cp-1, PRD1, PZE, SFS, Cp-5, Cp-7, PR4, PR5, PR722, L17, Φ21, or the like. For nomenclature, see also, Meijer et al. (2001) "Φ29 Family of Phages" Microbiology and Molecular Biology Reviews, 65(2):261-287. Suitable polymerases are described, for example, in U.S. Patent application publications 2007-0196846, 2008-0108082, 2010-0075332, 2010-0093555, 2010-0112645, 2011-0189659, 2012-0034602, 2013-0217007, 2014-0094374, and 2014-0094375.

In further embodiments, the polymerase enzyme used in the methods of the invention includes RNA dependent DNA polymerases or reverse transcriptases. Suitable reverse transcriptase enzymes include HIV-1, M-MLV, AMV, and Telomere Reverse Transcriptase. Reverse transcriptases also allow for the direct sequencing of RNA substrates such as messenger RNA, transfer RNA, non-coding RNA, ribosomal RNA, micro RNA or catalytic RNA.

The polymerase enzymes of use in the present invention generally require a primer. While in most cases an oligonucleotide primer is used, in some cases a protein such as a terminal protein can acts as a primer. Oligonucleotide primers are generally complementary to a portion of the template nucleic acid. The primers can comprise naturally occurring RNA or DNA oligonucleotides. The primers may also be synthetic analogs. The primers may have alternative backbones as described above for the nucleic acids of the invention. The primer may also have other modifications, such as the inclusion of heteroatoms, the attachment of labels, such as dyes, or substitution with functional groups which will still allow for base pairing and for recognition by the enzyme. Primers can select tighter binding primer sequences, e.g., GC rich sequences, as well as employ primers that include within their structure non-natural nucleotides or nucleotide analogs, e.g., peptide nucleic acids (PNAs) or locked nucleic acids (LNAs), that can demonstrate higher affinity pairing with the template. The primer can also be selected to influence the kinetics of the polymerase reaction.

IV. Applications for Methods and Compositions of the Invention: Sequencing

The methods, devices, and compositions of the invention are particularly useful for single molecule sequencing methods, and specifically single molecule sequencing by incorporation in real time, because the present invention provides a way to efficiently remove free polymerases that might introduce errors or noise into such sequencing reactions.

In aspects of the methods described herein that use protease treatment at some point in the process to enrich the loading compositions for polymerase enzyme complexes, subsequent sequencing reactions that are conducted once the enriched loading composition is distributed onto a substrate may further be conducted in the presence of a protease inhibitor in order to prevent the protease from interfering with components of the sequencing reaction mixture. Protease inhibitors are known in the art and would be chosen based on the nature of the protease used during the enrichment process.

In general and as will be discussed in more detail below, sequencing reactions using the enriched compositions described herein can include a number of different processes, including sequencing by synthesis processes. Regardless of the particular sequencing method used, the methods described herein will generally include a step of exposing a composition comprising a polymerase enzyme complex to a protease, e.g., in the presence of a non-catalytic metal ion and a first set of one or more nucleotides or nucleotide analogs and/or in the presence of a non-hydrolyzable nucleotide analog, then removing or inactivating the protease, and then determining a nucleotide sequence of at least a portion of the template. The non-catalytic metal ion and/or non-hydrolyzable analog present in the composition during the protease enrichment step may optionally be removed prior to the sequence determining reaction by washing with buffers or other mixtures (such as sequencing reaction mixtures) that do not contain the non-catalytic metal ion or non-hydrolyzable analog.

The step of determining the nucleotide sequence can include providing a catalytic metal ion in order to activate the polymerase. The catalytic metal ion can include without limitation magnesium or manganese.

In further embodiments, the determining the nucleotide sequence includes disposing the loading composition on a substrate. As is discussed in further detail above, the loading composition may be enriched to favor polymerase enzyme complexes using protease enrichment alone or in combination with other purification methods. As is also discussed herein, those one or more enrichment steps may take place prior to the disposing of the loading composition on a substrate or after (i.e., the protease treatment may occur on the surface of the substrate). Once the composition has been enriched for polymerase enzyme complexes, a second set of one or more nucleotides or nucleotide analogs is provided, and a polymerization reaction is performed in which the polymerase replicates at least a portion of the template in a template-dependent manner. In such a reaction, the one or more nucleotides or nucleotide analogs from that second set are incorporated into the resulting nucleic acid, and identifying a time sequence of incorporation of the one or more nucleotide or nucleotide analogs into the resulting nucleic acid provides sequence information on the template.

In certain embodiments, the first set of nucleotides or nucleotide analogs that is present during the enrichment steps may or may not be labeled. In further embodiments, the second set of nucleotides or nucleotide analogs that is present during the steps of determining the nucleotide sequence may or may not be labeled. For real time single molecule sequencing methods, the set of nucleotides or nucleotide analogs employed generally do include labels to allow detection of each nucleotide or nucleotide analog as it is incorporated into the nascent strand produced by the polymerase.

In further embodiments, the sequencing reactions are conducted in the presence of a protease inhibitor. Such protease inhibitors are known in the art and include any molecules known to interfere with the function of or result in the inactivation of the protease used during the enrichment process. Inclusion of the protease inhibitor can help prevent interference of the protease with components of the reaction mixture and also prevents digestion of the polymerase as it progresses into the active form for progression of the sequencing reaction. In certain embodiments, the protease used in the enrichment step is trypsin, and thus in further embodiments, the subsequent sequencing reaction could be conducted in the presence of a trypsin inhibitor. Similarly, any other protease that may be used in the enrichment step may in a subsequent sequencing reaction be inactivated by the appropriate protease inhibitor. In other embodiments, the protease inhibitor is added and optionally removed (e.g., by washing) before the sequencing reaction is initiated.

In some aspects, the present invention includes methods of analyzing the sequence of template nucleic acids associated with the polymerase enzyme complexes discussed herein. In such aspects, the sequence analysis employs template dependent synthesis in identifying the nucleotide sequence of the template nucleic acid. Nucleic acid sequence analysis that employs template dependent synthesis identifies individual bases, or groups of bases, as they are added during a template mediated synthesis reaction, such as a primer extension reaction, where the identity of the base is required to be complementary to the template sequence to which the primer sequence is hybridized during synthesis. Other such processes include ligation driven processes, where oligo- or polynucleotides are complexed with an underlying template sequence, in order to identify the sequence of nucleotides in that sequence. Typically, such processes are enzymatically mediated using nucleic acid polymerases, such as DNA polymerases, RNA polymerases, reverse transcriptases, and the like, or other enzymes such as in the case of ligation driven processes, e.g., ligases.

Sequence analysis using template dependent synthesis can include a number of different processes. For example, in embodiments utilizing sequence by synthesis processes, individual nucleotides or nucleotide analogs are identified iteratively as they are added to the growing primer extension product.

For sequencing processes that rely upon monitoring of the incorporation of nucleotides into growing nascent strands being synthesized by the complex, the progress of the reaction through these steps can of significant importance. In particular, for certain "real-time" nucleotide incorporation monitoring processes, the detectability of the incorporation event is improved based upon the amount of time the nucleotide is incorporated into and retained within the synthesis complex during its ultimate incorporation into a primer extension product. By way of example, in certain exemplary processes, the presence of the nucleotide in the synthesis complex is detected either by virtue of a focused observation of the synthesis complex, or through the use of interactive labeling techniques that produce characteristic signals when the nucleotide is within the synthesis complex. See, e.g., Levene, et al., Science 299:682-686, January 2003, and Eid, J. et al., Science, 323(5910), 133-138 (2009), the full disclosures of which are incorporated herein by reference in their entirety for all purposes.

In further aspects, the methods of the present invention include steps from any single molecule sequencing methods known in the art. See, e.g., Rigler, et al., DNA-Sequencing at the Single Molecule Level, Journal of Biotechnology, 86(3): 161 (2001); Goodwin, P. M., et al., Application of Single Molecule Detection to DNA Sequencing. Nucleosides & Nucleotides, 16(5-6): 543-550 (1997); Howorka, S., et al., Sequence-Specific Detection of Individual DNA Strands using Engineered Nanopores, Nature Biotechnology, 19(7): 636-639 (2001); Meller, A., et al., Rapid Nanopore Discrimination Between Single Polynucleotide Molecules, Proceedings of the National Academy of Sciences of the United States of America, 97(3): 1079-1084 (2000); Driscoll, R. J., et al., Atomic-Scale Imaging of DNA Using Scanning Tunneling Microscopy. Nature, 346(6281): 294-296 (1990).

In further embodiments, methods of single molecule sequencing known in the art include detecting individual nucleotides as they are incorporated into a primed template, i.e., sequencing by synthesis. Such methods often utilize exonucleases to sequentially release individual fluorescently labeled bases as a second step after DNA polymerase has formed a complete complementary strand. See Goodwin et al., "Application of Single Molecule Detection to DNA Sequencing," Nucleos. Nucleot. 16: 543-550 (1997).

In general, for sequencing methods utilizing compositions of the present invention, individual polymerase compositions are provided within separate discrete regions of a support. For example, in some cases, individual complexes may be provided within individual confinement structures, including nanoscale structures such as nanowells. In further examples, zero-mode waveguide cores or any of the reaction regions discussed above in the stepwise sequencing section serve as the reaction regions for sequencing methods utilizing compositions of the present invention. Examples of waveguides and processes for immobilizing individual complexes therein are described in, e.g., Published International Patent Application No. WO 2007/123763, the full disclosure of which is incorporated herein by reference in its entirety for all purposes and in particular for all teachings related to providing individual complexes into individual confinement structures. In some cases the complexes can be provided onto or proximal to structures or regions that allow for electronic single molecule sequencing. Such structures can include nanoscale electronic structures such as electrodes, capacitors, or field effect transducers (nanoFETs). NanoFETs include those having carbon nanotube gates. Such structures and their use for single molecule sequencing are described, for example, in U.S. Patent Application Publication No. 2015/0065353 which is incorporated herein in its entirety for all purposes and in particular for all teachings related to structures for use in single molecule sequencing.

Incorporation of labeled nucleotide analogs by polymerases is particularly useful in a variety of different nucleic acid analyses, including real-time monitoring of DNA polymerization. The label can itself be incorporated, or more preferably, can be released during incorporation of the analog. For example, analog incorporation can be monitored in real time by monitoring label release during incorporation of the analog by the polymerase. The portion of the analog that is incorporated can be the same as a natural nucleotide, or can include features of the analog that differ from a natural nucleotide.

In general, label incorporation or release can be used to indicate the presence and composition of a growing nucleic acid strand, e.g., providing evidence of template replication/amplification and/or sequence of the template. Signaling from the incorporation can be the result of detecting labeling groups that are liberated from the incorporated analog, e.g., in a solid phase assay, or can arise upon the incorporation reaction. For example, in the case of FRET labels where a bound label is quenched and a free label is not, release of a label group from the incorporated analog can give rise to a fluorescent signal. Alternatively, the enzyme may be labeled with one member of a FRET pair proximal to the active site, and incorporation of an analog bearing the other member will allow energy transfer upon incorporation. The use of enzyme bound FRET components in nucleic acid sequencing applications is described, e.g., in U.S. Patent Application Publication No. 2003/0044781, incorporated herein by reference.

In one example reaction of interest, a polymerase reaction can be isolated within an extremely small observation volume that effectively results in observation of individual polymerase molecules. As a result, the incorporation event provides observation of an incorporating nucleotide analog that is readily distinguishable from non-incorporated nucleotide analogs. In a preferred aspect, such small observation volumes are provided by immobilizing the polymerase enzyme within an optical confinement, such as a Zero Mode Waveguide (ZMW). For a description of ZMWs and their application in single molecule analyses, and particularly nucleic acid sequencing, see, e.g., U.S. Patent Application Publication No. 2003/0044781 and U.S. Pat. No. 6,917,726, each of which is incorporated herein by reference in its entirety for all purposes. See also Levene et al. (2003) "Zero-mode waveguides for single-molecule analysis at high concentrations" Science 299:682-686, Eid et al. (2009) "Real-time DNA sequencing from single polymerase molecules" Science 323:133-138, and U.S. Pat. Nos. 7,056,676, 7,056,661, 7,052,847, and 7,033,764, the full disclosures of which are incorporated herein by reference in their entirety for all purposes.

In general, a polymerase enzyme is complexed with the template strand in the presence of one or more nucleotides and/or one or more nucleotide analogs. For example, in certain embodiments, labeled analogs are present representing analogous compounds to each of the four natural nucleotides, A, T, G and C, e.g., in separate polymerase reactions, as in classical Sanger sequencing, or multiplexed together, e.g., in a single reaction, as in multiplexed sequencing approaches. When a particular base in the template strand is encountered by the polymerase during the polymerization reaction, it complexes with an available analog that is complementary to such nucleotide, and incorporates that analog into the nascent and growing nucleic acid strand. In one aspect, incorporation can result in a label being released, e.g., in polyphosphate analogs, cleaving between the α and β phosphorus atoms in the analog, and consequently releasing the labeling group (or a portion thereof). The incorporation event is detected, either by virtue of a longer presence of the analog and, thus, the label, in the complex, or by virtue of release of the label group into the surrounding medium. Where different labeling groups are used for each of the types of analogs, e.g., A, T, G or C, identification of a label of an incorporated analog allows identification of that analog and consequently, determination of the complementary nucleotide in the template strand being processed at that time. Sequential reaction and monitoring permits real-time monitoring of the polymerization reaction and determination of the sequence of the template nucleic acid. As noted above, in particularly preferred aspects, the polymerase enzyme/ template complex is provided immobilized within an optical confinement that permits observation of an individual complex, e.g., a zero mode waveguide. For additional information on single molecule sequencing monitoring incorporation of phosphate-labeled analogs in real time, see, e.g., Eid et al. (2009) "Real-time DNA sequencing from single polymerase molecules" Science 323:133-138.

In a first exemplary technique, a nucleic acid synthesis complex, including a polymerase enzyme, a template sequence and a complementary primer sequence, is provided immobilized within an observation region that permits illumination and observation of a small volume that includes the complex without excessive illumination of the surrounding volume. By illuminating and observing only the volume immediately surrounding the complex, one can readily identify fluorescently labeled nucleotides that become incorporated during that synthesis, as such nucleotides are retained within that observation volume by the polymerase for longer periods than those nucleotides that are simply randomly diffusing into and out of that volume. In particular, when a nucleotide is incorporated into DNA by the polymerase, it is retained within the observation volume for a prolonged period of time, and upon continued illumination yields a prolonged fluorescent signal. By comparison, randomly diffusing and not incorporated nucleotides remain within the observation volume for much shorter periods of time, and thus produce only transient signals, many of which go undetected due to their extremely short duration.

In particularly preferred exemplary systems, the confined illumination volume is provided through the use of arrays of optically confined apertures termed zero mode waveguides (ZMWs). See, e.g., U.S. Pat. No. 6,917,726, which is incorporated herein by reference in its entirety for all purposes. For sequencing applications, the DNA polymerase is typically provided immobilized upon the bottom of the ZMW, although another component of the complex (e.g., a primer or template) is optionally immobilized on the bottom of the ZMW to localize the complex. See, e.g., Korlach et al. (2008) PNAS U.S.A. 105(4):1176-1181 and US patent application publication 2008-0032301, each of which is incorporated herein by reference in its entirety for all purposes.

In operation, the fluorescently labeled nucleotides (e.g., analogs corresponding to A, C, G and T) bear one or more fluorescent dye groups on a terminal phosphate moiety that is cleaved from the nucleotide upon incorporation. As a result, synthesized nucleic acids do not bear the build-up of fluorescent labels, as the labeled polyphosphate groups diffuse away from the complex following incorporation of the associated nucleotide, nor do such labels interfere with the incorporation event. See, e.g., Korlach et al. (2008) Nucleosides, Nucleotides and Nucleic Acids 27:1072-1083.

In a second exemplary technique, the immobilized complex and the nucleotides to be incorporated are each provided with interactive labeling components. Upon incorporation, the nucleotide borne labeling component is brought into sufficient proximity to the complex borne (or complex proximal) labeling component, such that these components produce a characteristic signal event. For example, the polymerase may be provided with a fluorophore that provides fluorescent resonant energy transfer (FRET) to appropriate acceptor fluorophores. These acceptor fluorophores are provided upon the nucleotide to be incorporated, where each type of nucleotide bears a different acceptor fluorophore, e.g., that provides a different fluorescent signal. Upon incorporation, the donor and acceptor are brought close enough together to generate energy transfer signal. By providing different acceptor labels on the different types of nucleotides, one obtains a characteristic FRET-based fluorescent signal for the incorporation of each type of nucleotide, as the incorporation is occurring.

In a related aspect, a nucleotide analog may include two interacting fluorophores that operate as a donor/quencher pair, where one member is present on the nucleobase or other retained portion of the nucleotide, while the other member is present on a phosphate group or other portion of the nucleotide that is released upon incorporation, e.g., a terminal phosphate group. Prior to incorporation, the donor and quencher are sufficiently proximal on the same analog as to provide characteristic signal quenching. Upon incorporation and cleavage of the terminal phosphate groups, e.g., bearing a donor fluorophore, the quenching is removed and the resulting characteristic fluorescent signal of the donor is observable.

In exploiting the foregoing processes, where the incorporation reaction occurs too rapidly, it may result in the incorporation event not being detected, i.e., the event speed exceeds the detection speed of the monitoring system. The missed detection of incorporated nucleotides can lead to an increased rate of errors in sequence determination, as omissions in the real sequence. In order to mitigate the potential for missed pulses due to short reaction or product release times, in one aspect, the current invention can result in increased reaction and/or product release times during incorporation cycles. Similarly, very short interpulse distances can occasionally cause pulse merging. An advantage of employing polymerases with reduced reaction rates, e.g., polymerases exhibiting decreased rates and/or two slow-step kinetics as described in US patent application publications 2009-0286245 and 2010-0112645, is an increased frequency of longer, detectable, binding events. This advantage may also be seen as an increased ratio of longer, detectable pulses to shorter, non-detectable pulses, where the pulses represent binding events.

The sequencing processes, e.g., using the substrates described above and the compositions of the invention, are generally exploited in the context of a fluorescence optical system that is capable of illuminating the various complexes on the substrate, and obtaining, detecting and separately recording fluorescent signals from these complexes. Such systems typically employ one or more illumination sources that provide excitation light of appropriate wavelength(s) for the labels being used. An optical train directs the excitation light at the reaction region(s) and collects emitted fluorescent signals and directs them to an appropriate detector or detectors. Additional components of the optical train can provide for separation of spectrally different signals, e.g., from different fluorescent labels, and direction of these separated signals to different portions of a single detector or to different detectors. Other components may provide for spatial filtering of optical signals, focusing and direction of the excitation and or emission light to and from the substrate. An exemplary system is also described in Lundquist et al., Published U.S. Patent Application No. 2007-0036511, Optics Letters, Vol. 33, Issue 9, pp. 1026-1028, the full disclosure of which is incorporated herein by reference in its entirety for all purposes.

Fluorescence reflective optical trains can be used in the applications of the systems of the invention. For a discussion on the advantages of such systems, see, e.g., U.S. patent application Ser. No. 11/704,689, filed Feb. 9, 2007, Ser. No. 11/483,413, filed Jul. 7, 2006, and Ser. No. 11/704,733, filed Feb. 9, 2007, the full disclosures of which are incorporated herein by reference in their entirety for all purpose.

In the context of the nucleic acid sequencing methods described herein, it will be appreciated that the signal sources each represent sequencing reactions, and particularly, polymerase mediated, template dependent primer extension reactions, where in preferred aspects, each base incorporation event results in a prolonged illumination (or localization) of one of four differentially labeled nucleotides being incorporated, so as to yield a recognizable pulse (peak) that carries a distinguishable spectral profile or color.

In further embodiments, compositions of the present invention are utilized in sequencing methods utilizing nanopores. In exemplary embodiments, enzymes are attached to the scaffold and then loaded into a nanopore—the nanopore comprises binding moieties complementary to reaction moieties on the scaffold. In this way, a single enzyme is loaded into each nanopore. In certain embodiments, the scaffolds and their attached enzymes are attached proximal to the nanopore. As will be appreciated, helicases and exonucleases as well as polymerases can be used in nanopore sequencing. Protease treatment can remove free enzyme from complexes of a nucleic acid to be sequenced and a helicase, exonuclease, or other enzyme prior to nanopore sequencing, by treatment as described herein for removal of free enzyme from polymerase complexes. Methods of nanopore sequencing are known in the art and disclosed for example in US Published App. Nos. 2013/0327644 and 2014/0051068, which are hereby incorporated by reference for all purposes and in particular for all teachings, written description, figures and figure legends related to nanopore sequencing.

The present invention can further include computer implemented processes, and/or software incorporated onto a computer readable medium instructing such processes, as set forth in greater detail below. As such, signal data generated by the reactions and optical systems described above, is input or otherwise received into a computer or other data processor, and subjected to one or more of the various process steps or components set forth below. Once these processes are carried out, the resulting output of the computer implemented processes may be produced in a tangible or observable format, e.g., printed in a user readable report, displayed upon a computer display, or it may be stored in one or more databases for later evaluation, processing, reporting or the like, or it may be retained by the computer or transmitted to a different computer for use in configuring subsequent reactions or data processes.

Computers for use in carrying out the processes of the invention can range from personal computers such as PC or MacIntosh® type computers running Intel Pentium or Duo-Core processors, to workstations, laboratory equipment, or high speed servers, running UNIX, LINUX, Windows®, or other systems. Logic processing of the invention may be performed entirely by general purposes logic processors (such as CPU's) executing software and/or firmware logic instructions; or entirely by special purposes logic processing circuits (such as ASICs) incorporated into laboratory or diagnostic systems or camera systems which may also include software or firmware elements; or by a combination of general purpose and special purpose logic circuits. Data formats for the signal data may comprise any convenient format, including digital image based data formats, such as JPEG, GIF, BMP, TIFF, or other convenient formats, while video based formats, such as avi, mpeg, mov, rmv, or other video formats may be employed. The software processes of the invention may generally be programmed in a variety of programming languages including, e.g., Matlab, C, C++, C#, NET, Visual Basic, Python, JAVA, CGI, and the like.

In some cases, the compositions, methods, and systems of the invention can be used as part of an integrated sequencing system, for example, as described in US 20120014837—Illumination of Integrated Analytical Systems, US 20120021525—Optics Collection and Detection System and Method, US 20120019828—Integrated Analytical System and Method, 61/660,776 filed Jun. 17, 2012—Arrays of Integrated Analytical Devices and Methods for Production, and US 20120085894—Substrates and Optical Systems and Methods of Use Thereof which are incorporated herein by reference in their entirety for all purposes.

In certain embodiments, the sequencing compositions described herein will be provided in whole, or in part, in kit form enabling one to carry out the processes described herein. Such kits will typically comprise one or more components of the reaction complex, such as the polymerase enzyme and primer sequences. Such kits will also typically include buffers and reagents that provide the catalytic and non-catalytic metal co-factors, non-hydrolyzable nucleotide analogs, proteases, protease inhibitors, and/or the like employed in the processes described herein. The kits will also optionally include other components for carrying out sequencing applications in accordance with those methods described herein. In particular, such kits may include ZMW array substrates for use in observing individual reaction complexes as described herein.

In further exemplary embodiments, kits of the invention include (alone, or in any combination with the above described components of kits of the invention) components for use in the loading methods described herein. Such components may include in any combination one or more of the following: standard buffer for covering the surface, high density loading solution, polymerase enzymes, nucleic acid templates, primer sequences, particles for cleaning the high density loading solution, and any other composition described herein associated with loading polymerase compositions to a surface and/or conducting a sequencing reaction.

In addition to the various components set forth above, the kits will typically include instructions for combining the various components in the amounts and/or ratios set forth herein, to carry out the desired processes, as also described or referenced herein, e.g., for performing sequence by incorporation reactions and/or loading methods.

V. Substrates and Surfaces

Any of the loading compositions described herein can be distributed onto a substrate for enrichment treatments (such as the protease treatment described in detail above) and/or for further analyses such as sequencing reactions. Substrates of use in methods described herein are known in the art and discussed herein, and as will be appreciated, any of the substrates discussed herein can be used in any combination for any embodiment of a sequencing reaction and for any embodiment of the enriched compositions discussed herein. In exemplary embodiments, methods of sequencing of the invention utilize substrates that include one or more reaction regions (also referred to herein as "reaction chambers" and "array regions") arranged in the form of an array on an inert substrate material, also referred to herein as a "solid support" or "surface", that allows for combination of the reactants in a sequencing reaction in a defined space and for detection of the sequencing reaction event. A reaction region can be a localized area on the substrate material that facilitates interaction of reactants, e.g., in a nucleic acid sequencing reaction. A reaction region may in certain embodiments be a nanoscale well (also referred to herein as a nanowell), and in further embodiments the nanowell is a ZMW. A nanoscale well typically has dimensions in the nanometer range, i.e., less than 1 micrometer. In some embodiments, a nanoscale well has a cross-sectional diameter of less than 1000, 900, 800, 700, 600, or 500 nm, e.g., less than 400, 350, 300, 250, or 200 nm. In some embodiments, a nanoscale well has a depth of less than 1000, 900, 800, 700, 600, or 500 nm, e.g., less than 400, 350, 300, 250, or 200 nm. As discussed herein, the sequencing reactions contemplated by the invention can in some embodiments occur on numerous individual nucleic acid samples in tandem, in particular simultaneously sequencing numerous nucleic acid samples, e.g., derived from genomic and chromosomal DNA. The apparatus of the invention can therefore include an array having a sufficient number of array regions/reaction regions to carry out such numerous individual sequencing reactions. In one embodiment, the array comprises at least 1,000 reaction regions. In another embodiment, the array comprises greater than 400,000 reaction regions, preferably between 400,000 and 20,000,000 reaction regions. In a more preferred embodiment, the array comprises between 1,000,000 and 16,000,000 reaction regions, e.g., 1,000,000, 2,000,000, 3,000,000, 4,000,000, 5,000,000, 6,000,000, 7,000,000, 8,000,000, 9,000,000, or 10,000,000 reaction regions.

The reaction regions on the array may take the form of a cavity or well in the substrate material, having a width and depth, into which reactants can be deposited. One or more of the reactants typically are bound to the substrate material in the reaction region and the remainder of the reactants are in a medium which facilitates the reaction and which flows through the reaction region. When formed as cavities or wells, the chambers are preferably of sufficient dimension and order to allow for (i) the introduction of the necessary reactants into the chambers, (ii) reactions to take place within the chamber and (iii) inhibition of mixing of reactants between chambers. The shape of the well or cavity is preferably circular or cylindrical, but can be multisided so as to approximate a circular or cylindrical shape. In another embodiment, the shape of the well or cavity is substantially hexagonal. The cavity can have a smooth wall surface. In an additional embodiment, the cavity can have at least one irregular wall surface. The cavities can have, e.g., a planar bottom or a concave bottom. In some embodiments, the reaction regions have a width in one dimension of between 100-500 nm, 200-400 nm, 100-300 nm, 100-200 nm, 150-200 nm. The reaction regions optionally have a depth that is between 0.25 and 5 times the width in one dimension of the reaction region.

Any material can be used as the solid support material, as long as the surface allows for stable attachment of polymerase enzyme complexes and optionally detection of nucleotide incorporation. The solid support material can be planar or can be cavitated, e.g., in a cavitated terminus of a fiber optic or in a microwell etched, molded, or otherwise micromachined into the planar surface, e.g. using techniques commonly used in the construction of microelectromechanical systems. See e.g., Rai-Choudhury, HANDBOOK OF MICROLITHOGRAPHY, MICROMACHINING, AND MICROFABRICATION, VOLUME 1: MICROLITHOGRAPHY, Volume PM39, SPIE Press (1997); Madou, CRC Press (1997), Aoki, Biotech. Histochem. 67: 98-9 (1992); Kane et al., Biomaterials. 20: 2363-76 (1999); Deng et al., Anal. Chem. 72:3176-80 (2000); Zhu et al., Nat. Genet. 26:283-9 (2000). In some embodiments, the solid support is optically transparent, e.g., glass.

Suitable substrates include chips having arrays of nanoscale wells or zero mode waveguides. Exemplary substrates include substrates having a metal or metal oxide layer on a silica-based layer, with nanoscale wells disposed through the metal or metal layer to or into the silica-based layer. Such substrates are described, for example in U.S. patent application Ser. Nos. 10/259,268, 14/187,198, 14/107,730, 13/920,037, and U.S. Pat. Nos. 8,994,946, 8,906,670, 8,993,307, 8,802,600, 7,907,800, and 7,302,146, which are incorporated herein by reference in their entirety for all purposes and in particular for all teachings related to substrates.

EXAMPLES

Example 1: Protease Treatment Removes Background Pulses from Free Polymerase

Protease treatment preferentially digests free polymerases over polymerases complexed with nucleic acids. For samples exposed to 5 µg/mL trypsin, the free form is consumed within the first minute, while the template-bound, ternary complex remains intact over a 20 minute time course (data not shown). This preferential digestion suggests that background signals and inaccuracies introduced by the activity of free polymerases can be reduced by treating loading compositions containing a mixture of free polymerases and polymerase enzyme complexes.

As shown in FIGS. 1 and 2, addition of protease reduces pulses from free polymerases back to control levels, indicating that most or all the free polymerases were degraded or rendered inactive by the protease In FIG. 1(a), low rates of background pulsing (fluorescent signals) were seen in the presence of a control reaction mix containing fluorescently labeled nucleotides but no polymerase. Upon addition of 40 pM polymerase (free polymerase not complexed with any nucleic acid templates), the observed pulse rate increased (FIG. 1(b)). Note that in the experiments pictured in FIG. 1, the polymerase was immobilized to a surface. As shown in FIG. 1(c), the pulse rate recovered to near control levels (as seen with the reaction-mix only) upon treatment with proteinase K (protK). In the experiments shown in FIG. 1(c), 5 µg/mL proteinase K was added to the mixture.

A similar result was seen with the use of the protease trypsin, as shown in FIG. 2. In the presence of reaction-mix only, very few pulses were seen (FIG. 2(a)). Upon addition of 50 pM free polymerase, pulsing activity increased, indicating the level of background signals that free polymerases can contribute (FIG. 2(b)). As shown in FIG. 2(c), the pulse rate recovered to near reaction-mix only values when the added polymerase was degraded by trypsin. There was a concentration dependence in the effect of the free polymerase on background pulses. As shown in FIG. 2(d), addition of 500 pM polymerase increased the pulse rate more than was seen with 50 pM polymerase. That increased pulse rate again decreased upon the addition of trypsin. (FIG. 2(e)). For the experiments in which trypsin was used, 10 µg/mL trypsin was added in a buffer to the polymerase mixture on the surface and incubated for 10 minutes. The trypsin was then removed with multiple washes of buffer not containing any trypsin. After removing the trypsin, a sequencing mixture was applied and pulses were measured in the same manner as for the panels in which no trypsin was added.

Example 2: Protease Treatment Improved Raw Accuracy

As shown in FIG. 3, sequencing reactions with a polymerase composition containing both free polymerases and polymerases complexed with a 1 kb template nucleic acid (1 kb SMRTbells™) produced sequencing data with a low raw accuracy (dashed line). Addition of trypsin for 10 minutes prior to sequencing increased the raw accuracy significantly (solid line). As with the experiments described in Example 1, 10 µg/mL trypsin was added in a buffer to the polymerase mixture on the surface and incubated for 10 minutes. The trypsin was then removed with multiple washes of buffer not containing any trypsin. After removing the trypsin, a sequencing mixture was applied and single molecule sequencing data generated.

Example 3: Protease Treatment Improved Signal to Noise

Figure 4:
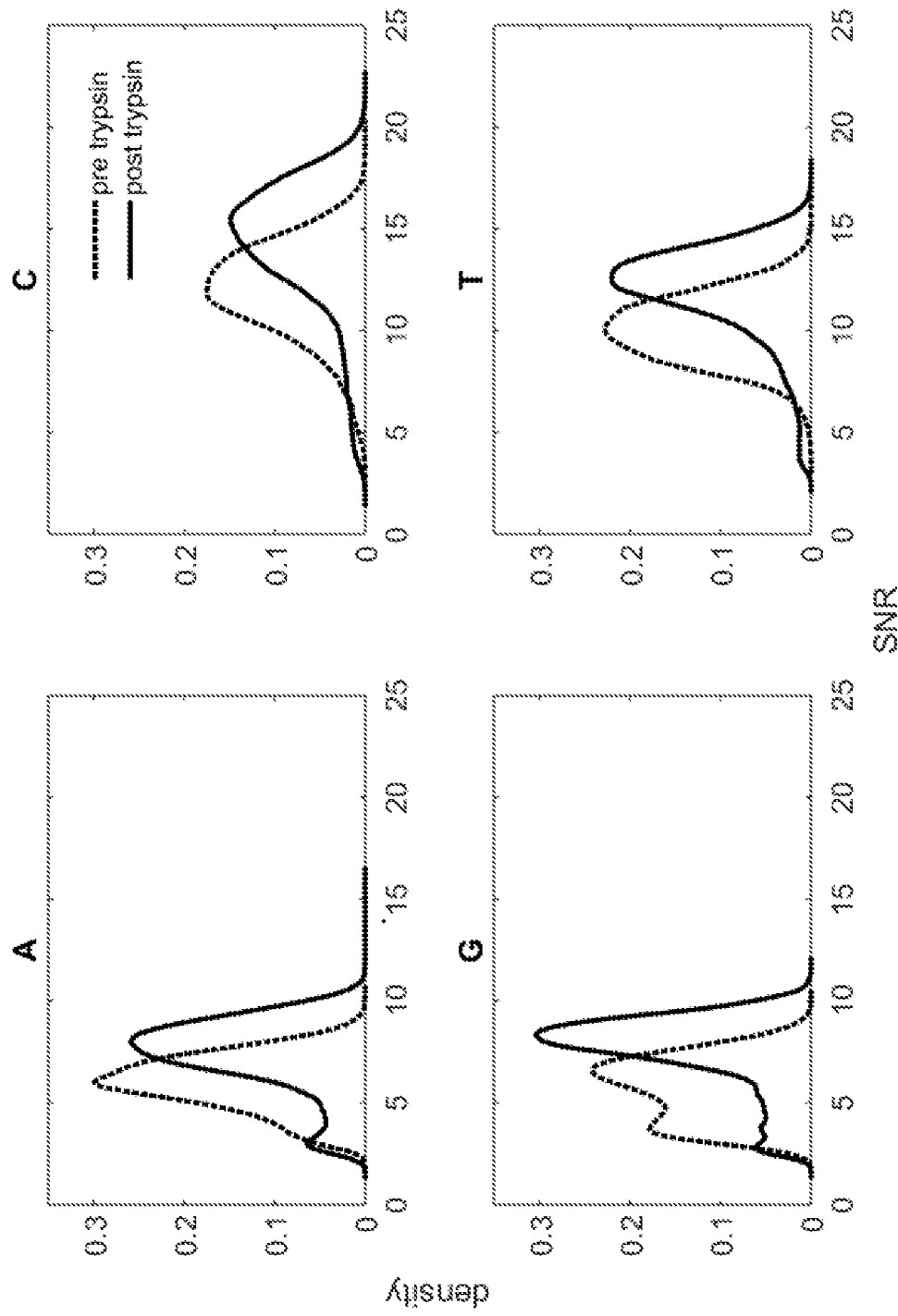
FIG. 4 shows data on signal to noise in sequencing data from polymerase compositions on a substrate before (dashed line) and after (solid line) treatment with trypsin—all four bases (A, C, T, G) showed improved signal to noise after the trypsin treatment.

As with the raw accuracy improvement described in Example 3, treatment with a protease also improved signal to noise ratio for individual bases in a sequencing reaction. In FIG. 4, signal to noise ratio (SNR) is shown for individual bases before and after protease treatment to remove free polymerases. As seen in FIG. 4, for all four bases (A, C, T and G), signal to noise was clearly improved after protease treatment—compare signal to noise for polymerase compositions prior to treatment with protease (dashed lines) and after treatment with protease (solid lines). For the experiments depicted in FIG. 4, the templates were 1 kb nucleic acid templates, and the protease used was trypsin. As with the experiments described in previous examples, 10 µg/mL trypsin was added in a buffer to the polymerase mixture on the surface and incubated for 10 minutes. The trypsin was then removed with multiple washes of buffer not containing any trypsin. After removing the trypsin, a sequencing mixture was applied and single molecule sequencing data generated.

The present specification provides a complete description of the methodologies, systems and/or structures and uses thereof in example aspects of the presently-described technology. Although various aspects of this technology have been described above with a certain degree of particularity, or with reference to one or more individual aspects, those skilled in the art could make numerous alterations to the disclosed aspects without departing from the spirit or scope of the technology hereof. Since many aspects can be made without departing from the spirit and scope of the presently described technology, the appropriate scope resides in the claims hereinafter appended. Other aspects are therefore contemplated. Furthermore, it should be understood that any operations may be performed in any order, unless explicitly claimed otherwise or a specific order is inherently necessitated by the claim language. It is intended that all matter contained in the above description shall be interpreted as illustrative only of particular aspects and are not limiting to the embodiments shown. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all published references and patent documents referred to in this disclosure are incorporated herein by reference in their entirety for all purposes. Changes in detail or structure may be made without departing from the basic elements of the present technology as defined in the following claims.

What is claimed:

1. A method for enriching a loading composition for polymerase enzyme complexes, the method comprising:
    (a) providing a loading composition comprising free polymerases and polymerase enzyme complexes, wherein the polymerase enzyme complexes are in an inactive form, and wherein each polymerase enzyme complex comprises a polymerase enzyme bound to a nucleic acid template;
    (b) applying a protease to the loading composition, which protease is more effective against the free polymerases than against polymerases in the polymerase enzyme complexes, and performing limited proteolytic digestion to reduce the amount of free polymerase relative to the amount of polymerase enzyme complex present in the composition, thereby enriching the loading composition for polymerase enzyme complexes; and
    (c) distributing the loading composition onto a substrate to provide a loaded substrate.

2. The method of claim 1, wherein the loading composition is purified to enhance the loading composition for polymerase enzyme complexes.

3. The method of claim 1, wherein applying step (b) is conducted after distributing step (c).

4. The method of claim 1, wherein the protease comprises an endopeptidase.

5. The method of claim 1, wherein the protease comprises trypsin.

6. The method of claim 1, wherein the substrate comprises an array of nanoscale wells.

7. The method of claim 1, wherein the distributing step (c) comprises immobilizing the polymerase enzyme complexes to the substrate.

8. The method of claim 7, wherein the polymerase enzyme complexes comprise a reactive element, and the immobilizing occurs through an interaction of the reactive element and a binding site on the substrate.

9. The method of claim 8, wherein the reactive element comprises streptavidin and the binding site comprises biotin.

10. The method of claim 8, wherein the reactive element is resistant to cleavage by the protease.

11. The method of claim 1, wherein the inactive form of the polymerase enzyme complexes is maintained by including a non-catalytic metal ion in the loading composition.

12. The method of claim 11, wherein the non-catalytic metal ion is a member selected from the group consisting of: strontium, cobalt, tin, calcium, nickel, europium, barium, iron, and zinc.

13. The method of claim 1, wherein the loading composition comprises one or more nucleotides or nucleotide analogs.

14. The method of claim 1, wherein the inactive form of the polymerase enzyme complexes is maintained by including at least one non-hydrolyzable nucleotide analog in the loading composition.

15. The method of claim 1, comprising step (d) determining a nucleotide sequence of at least a portion of the template.

16. The method of claim 15, wherein determining the nucleotide sequence comprises:
(i) providing a sequencing reaction mixture to the loaded substrate, the sequencing reaction mixture comprising at least one catalytic metal ion and one or more nucleotides or nucleotide analogs;
(ii) performing a polymerization reaction in which the polymerase replicates at least a portion of the template in a template-dependent manner, whereby the one or more nucleotides or nucleotide analogs are incorporated into the resulting nucleic acid; and
(iii) identifying a time sequence of incorporation of the one or more nucleotides or nucleotide analogs into the resulting nucleic acid.

17. The method of claim 16, wherein the performing step (ii) is conducted in the presence of a protease inhibitor.

18. The method of claim 16, wherein the one or more nucleotide or nucleotide analogs are labeled nucleotides or nucleotide analogs.

19. The method of claim 1, wherein the substrate comprises nanopores.

20. A method for enriching a loading composition for enzyme complexes, the method comprising:
(a) providing a loading composition comprising free enzymes and enzyme complexes, wherein the enzyme complexes are in an inactive form;
(b) applying a protease to the loading composition, which protease is more effective against the free enzymes than against enzymes in the enzyme complexes, and performing limited proteolytic digestion to reduce the amount of free enzyme relative to the amount of enzyme complex present in the composition, thereby enriching the loading composition for enzyme complexes; and
(c) distributing the loading composition onto a substrate to provide a loaded substrate.

21. The method of claim 20, wherein the substrate comprises nanopores or an array of nanoscale wells.

* * * * *